United States Patent [19]
Loubser

[11] Patent Number: 6,106,509
[45] Date of Patent: Aug. 22, 2000

[54] CLOSED CIRCUIT AUTOLOGOUS SEQUESTRATION RESERVOIR SYSTEM

[76] Inventor: Paul G. Loubser, 302 Lakeglen Ct., Sugarland, Tex. 77478

[21] Appl. No.: 08/912,742

[22] Filed: Aug. 18, 1997

Related U.S. Application Data

[63] Continuation-in-part of application No. 08/598,688, Feb. 8, 1996, Pat. No. 5,658,271.
[51] Int. Cl.$^7$ ............................ A61B 19/00; A61M 37/00
[52] U.S. Cl. .......................... 604/410; 604/408; 604/4.01; 604/6.07; 604/6.1; 604/6.13; 604/6.14; 604/6.15; 604/6.16
[58] Field of Search .................................... 604/4–6, 408, 604/410–12

[56] References Cited

U.S. PATENT DOCUMENTS

| | | | |
|---|---|---|---|
| 4,424,190 | 1/1984 | Mather, III et al. | 422/46 |
| 5,658,271 | 8/1997 | Loubser | 604/410 |
| 5,728,087 | 3/1998 | Niedospial, Jr. | 604/408 |

FOREIGN PATENT DOCUMENTS

WO 94/23664  10/1994  WIPO ................................. 604/408

Primary Examiner—Mark O. Polutta
Assistant Examiner—Patricia Bianco
Attorney, Agent, or Firm—Harrison & Egbert

[57] ABSTRACT

An apparatus is provided for autologous sequestration of blood from a patient prior to, during and after surgery. Sequestered blood contained in an assembly of oxygenated blood collection bags is kept in fluid contact with the patient throughout surgery, thereby assuring continuity with the patient's circulatory system. The plurality of blood collection bags is interconnected with a corresponding plurality of valves which is interconnected with a plurality of flexible tubes which is attached to a patient's right atrium or a peripheral artery. Following induction of anesthesia in the operating room, a patient's blood is sequestered into a collection bag assembly which forms a closed circuit blood reservoir system. Collected blood during surgery trickles back into the patient's blood system, thereby emulating venous blood flow. The collection bags are agitated and oxygenated to promote the functionality and longevity of the platelets in the sequestered blood.

28 Claims, 14 Drawing Sheets

CLOSED CIRCUIT AUTOLOGOUS SEQUESTRATION RESERVOIR SYSTEM

RELATED APPLICATIONS

This application is a continuation-in-part of U.S. application Ser. No. 08/598,688 filed Feb. 8, 1996, U.S Pat. No. 5,658,271.

BACKGROUND OF THE INVENTION

This invention relates to blood transfusions, and more particularly relates to means and methods for autologous sequestration of blood.

As is well known by those skilled in the art, patients frequently lose blood during surgical procedures. Under circumstances in which such blood loss is excessive, blood must be replaced to avoid undue risk to the patient. Prerequisite blood transfusions are thus commonly administered prior to, during, and after surgical procedures and the like. Traditionally, blood banks have supplied various blood products to hospitals and the like according to the rules promulgated by the American Association of Blood Banks. Similarly, blood transfusion practices by physicians and in hospitals are routinely monitored by the Joint Commission on Accreditation of Healthcare Organizations.

Typically, blood products are donated by or received from family members or known or unknown individuals; such blood products are referred to as "allogeneic" products. During the 1980's, unfortunately, it was discovered that the nation's allogeneic blood supply was contaminated with the human immunodeficiency virus (HIV). This immediately heightened public awareness and caused concern among health care professionals, patients and the media related to safe administration of blood transfusions.

It will be appreciated by those skilled in the art, that in view of the dangers of HIV infection of allogeneic blood, current blood transfusion practices have become more conservative. Nevertheless, current blood testing practices are unable to prevent HIV contamination. Guidelines for administering blood transfusions have been reexamined and redefined. Safe and effective alternatives using allogeneic blood products have been explored, including synthetic blood substitutes, autotransfusion, acute normvolemic hemodilution, etc.

In an article entitled "Blood Transfusion-Induced Immunomodulation" and reviewing the immunomodulatory effects of transfusion therapy, Dennis F. Landers, Gary E. Hill, K. C. Wong and Ira J. Fox state that available data at least suggest that allogeneic blood products increase cancer recurrence after a potentially curative surgical resection. *Anesth Analg*, vol. 82, pp 187–204, 1996. The authors suggest a continued awareness of the risks associated with use of allogeneic blood and use of techniques which tend to reduce such risks such as lower transfusion trigger, intraoperative and postoperative readministration of shed blood, and preoperative autologous donation with or without erythropoietin.

For the use of allogeneic blood, of course, conventional blood bank practice is to collect blood from an acceptable donor in citrate to prevent coagulation. Several components are separated from the collected blood including packed red blood cells, platelets and plasma. It is also a common practice for plasma and platelets to be collected using pheresis techniques. As is well known by those skilled in the art, allogeneic whole blood is rarely used. The blood products collected at blood banks are then stored in accordance with shelf-life survivability expectations. Prior to administering allogeneic blood, the patient's blood is cross-matched to assure its compatibility with the patient's blood type.

The threshold for the actual administration of allogeneic blood by a physician anesthesiologist is presently uncertain. Prior to the current pervasive HIV-threat associated with allogeneic blood transfusions, packed red blood cell transfusions would commence when hemoglobin levels fell below 10 g/dl. But practitioners in the art currently are inclined to withhold such transfusions until hemoglobin levels fall below 6–8 g/dl, depending upon the patient's health. Obviously, an 80-year old patient having cardiovascular disease would be transfused sooner than a healthy 18-year old. See, e.g., the paper entitled "Severity of Anemia and Operative Mortality and Morbidity" by Jeffrey L. Carson, Roy M. Poses, Richard K. Spence and Gregory Bonavita published in *Lancet*, vol. 1, pp 727–729 in 1988. As will be appreciated by those skilled in the art, one unit of packed red blood cells typically increases the hemoglobin level by about 1 g/dl.

It is widely known that the transfusion of blood contaminated with HIV has caused thousands of cases of acquired immunodeficiency syndrome (AIDS). To reduce the risk of patients acquiring AIDS from transfused blood, allogeneic blood is routinely screened for the presence of HIV. But since the current ELISA, i.e., enzyme-linked immunosorbant assay, antibody test fails to detect donors infected with HIV during the so-called "immunologic window"—from 4 weeks to 14 months—wherein donors may be HIV-infected but test negative, the risk associated with transfusing 1 unit of allogeneic blood ranges from 1:153,000 to 1:61,000. See, M. P. Busch, at al., *New England Journal of Medicine*, vol. 325, pp 1–5, 1991.

Blood banks have been attempting to reduce these risks by using repeat, HIV-safe donors and by using donors designated by particular patients. But is not clear that using repeat or designated donors actually reduced the risk of HIV infection from allogeneic transfusions. Other infectious risks associated with use of allogeneic blood products include hepatitis, certain strains of gram negative bacteria which can cause septic shock, and immunosuppression which predisposes patients to increased risks of infection.

There have been several developments in the art to avoid the inherent disadvantages associated with using allogeneic blood products. For example, autologous predonation may be used by patients who donate their blood to a blood bank on a weekly basis prior to being subjected to surgery. Collection of as much as 4 units of whole blood may be scheduled as frequently as every 96 hours, provided that a patients hemoglobin must be at least 12.5 g/dl prior to each such phlebotomy. See, 21 C.F.R. § 640.3. While patients using predonation obviously have the benefit of using their own blood, there may be a problem due to "storage lesion" which develops with prolonged refrigeration of collected blood.

Another example is autotransfusion and intraoperative blood salvage, which may be used under circumstances in which extreme blood loss is anticipated. According to intraoperative blood salvage methodology, hemorrhaged blood is collected into an autotransfusion device, anticoagulated, washed and then recycled into the patient. Commonly used autotransfusion devices provide centrifugation to wash blood cells as the blood is collected. An inherent disadvantage with this method is that large amounts of citrate or heparin are mixed with the blood to avoid coagulation. As will also be understood by those skilled in the art, washed blood contains only red blood cells and is devoid of platelets or plasma. Practitioners in the art have also applied this technique postoperatively wherein blood is collected into canisters from chest tubes, and then filtered and administered back to the patient. Blood administered in this fashion is similar to serum having no fibrinogen.

As is known to those skilled in the art, heparin is commonly used during cardiac surgery to prevent coagulation of a patient's blood during cardiopulmonary bypass. Once anticoagulated, a patient's blood may be rapidly sequestered under aortic pressure. It will be understood, however, that once cardiopulmonary bypass commences, further sequestration is limited because of additional hemodilution engendered by this extra corporeal circuit. Furthermore, such a post-heparinization rapid blood sequestration procedure is apt to introduce significant risk, subjecting a patient to greater hemodynamic instability and to possible inadequate perfusion of the heart, brain, and kidneys. In the art, the apparatus used for this procedure is configured as an open circuit and fails to consider the beneficial affects of blood-warming.

Unfortunately, the impact of heparin upon blood has been observed to be fundamentally noxious to platelets. See, E. Saltzman, et al., "Thromboresistance of Heparin-Coated Surfaces," *Chemistry and Biology of Heparin*, editors: R. L. Lundblad et al, Elsevier North Holland, N.Y., pps. 435–447, 1981. According to some researchers, heparin produces a state of "platelet activation" W. D. Comper, *Heparin*, Gordon and Breach Science Publishers, New York, Chapter 7, "Extracellular Interactions," pps. 175–248, 1981, which causes platelets to aggregate or clump. In addition, activated platelets tend to degranulate thereby releasing substances including ADP, PF4, etc.; this has been called a "platelet release reaction." F. Fabris, et al, "The Effect of Heparins on Platelet Release Reaction," *Heparin, New Biochemical and Medical Aspects*, editors: I. Witt, Walter de Gruyter & Company, Berlin, pps. 207–225, 1982.

It has also been observed that platelets, once activated, notwithstanding disaggregating, suffer from impaired response to stimuli. See, e.g., S. N. Harris, et al, "Evaluation of Platelet Function During Autologous Function During Autologous Blood Donation," *Anesthesiology* 75:A1121, 1991. Thus, it is a limitation of the prior art that post-heparinization rapid blood sequestration procedures is inherently unsafe because of heparin's noxious affect upon platelets and the risk of hemodynamic instability. Other likely adverse affects upon platelets include heparin-induced transient or reversible thrombocytopenia, and heparin induced thrombocytopenia (HIT). While the incidence of these thrombocytopenia conditions are rare, the vulnerabilities associated with the use of heparin to promote rapid blood sequestration should be evident to those familiar with the art.

Another methodology for removing blood from a patient intraoperatively with the simultaneous administration of crystalloid or colloid to maintain normovolemia is acute normovolemic hemodilution. This technique is described by L. Sterling and H. L. Zauder in the article "Acute Normovolemic Hemodilution" published in Transfusion, vol. 31, pp 857–868, in 1991. A suitable volume of blood is collected into blood bags containing anticoagulant and stored for use during subsequent surgery. Generally, acute normovolemic hemodilution tends to reduce the amount of allogeneic blood used during a surgical procedure. Unfortunately, if such collected blood is not used within 6 hours of removal from a patient, A.A.B.B. rules stipulate that the collected blood must be refrigerated to minimize infection risks. See, 21 C.F.R. § 640.2.

As will be appreciated by practitioners in the art, the theoretical basis for the acute normovolemic hemodilution methodology is that it is advantageous to lose blood with a lower Hb/Hematocrit (Hct) than a higher Hb/Hct. For instance, if a patient with a Hct of 0.45 loses 1 liter of whole blood during a surgical procedure, then 450 ml of red blood cells have been lost. If, however, after acute normovolemic hemodilution has been performed, the Hct is reduced to 0.25, then only 250 ml of red blood cells have been lost. Simultaneously with acute normovolemic hemodilution, arterial oxygen content decreases, cardiac output increases as much as 36%, tissue extraction increases, and blood viscosity decreases. Since coronary blood flow is proportional to cardiac output, coronary blood flow increases concomitantly with increased cardiac output.

There is also evidence that these physiologic responses to acute normovolemic hemodilution may compromise patient safety by producing wall motion abnormalities and myocardial ischemica. See, e.g., the paper by J. Gillon published in *Transfusion*, vol. 34, pp. 269–271, 1994. But there are studies that indicate that patients may tolerate large amounts of intraoperative hemodilution. See, e.g., two papers published in *Anesth Analg*: by Fontana, et al., in vol. 80, pp. 219–225, 1995 and by Van Woerkens, et al., in vol. 75, pp. 818–821, 1992. Those skilled in the art have developed various formulas for calculating acute normovolemic hemodilution end-points and for calculating the Hb of collected blood.

It is also known in the transfusion art that there are religious objections to use of allogeneic blood. Jehovah's Witnesses refuse the administration of all allogeneic blood products. Accordingly, autologous predonation is incompatible with the beliefs of Jehovah's Witnesses: since blood leaves a patient's body for prolonged periods of time before being used, predonation violates the sacred principle that blood must not be consumed or that there must be abstinence from blood. It should be noted, however, that the extra corporeal circulation provided by a heart-lung apparatus during cardiac surgery is acceptable to Jehovah's Witnesses because a patient's blood is diverted via cannulae to an oxygenator and then pumped back to the patient via another set of cannulae. Thus, this extra corporeal circulation functions as an extension of a patient's circulatory system, sustaining continuous connection therewith. That is, a patient's blood circulates through a closed circuit integral with the patient's own circulatory system.

While autotransfusion and intraoperative blood salvage methodologies generally function as extensions of a patient's circulatory system, blood exiting from a surgical wound would appear to be divorced from the closed circuit. By adapting current autotransfusion devices and connecting such devices prior to surgery, blood that is aspirated or suctioned from a surgical wound is kept within the closed circuit.

Similarly, during acute normovolemic hemodilution, if there is an interruption in the circulation of blood, wherein blood is temporarily collected into blood bags, then the closed circuit aspect is destroyed. To be compatible with the beliefs of Jehovah's Witnesses, there must at least be a constant, albeit slow, trickle of blood throughout the extended circulatory system.

There have been improvements in the art to enable safer and less objectionable transfusion methodologies during surgical procedures. For instance, in U.S. Pat. Nos. 4,047, 526 and 4,006,745, Reynolds et al. and Sorenson et al. teach autologous blood systems that first suck blood from the surgical field and then filter and return this blood to the patient. As will be appreciated by those skilled in the art, these autologous techniques cannot be administered in the presence of infection because of likely contamination of the patient's blood. An additional disadvantage of the methods disclosed by Reynolds and Sorenson is that no consideration is made of the possibility that various components of a patient's blood may be damaged by the suction process nor how coagulation aspects and platelets may be activated or consumed, while being aspirated from a surgical field.

Sharp, in U.S. Pat. No. 4,838,861 teaches blood preservation by ultrahemodilution wherein a patient's blood is withdrawn, diluted and then processed prior to be returned to the patient. But Sharp does not contemplate a closed circuit wherein a patient's circulation is uninterrupted. Similarly, in U.S. Pat. No. 5,078,677, Gentelia et al. teach an apparatus for postoperatively collecting a patient's blood and then for the reinfusion of this blood into the patient. Continuity with the patient's circulatory system appears to be interrupted when the reinfusion apparatus is disconnected from the patient's chest drainage section.

Roth et al. disclose synthetic oxygen carriers in the context of acute normovolemic hemodilution in U.S. Pat. No. 5,344,393. More particularly, Roth's perflubron carriers are intended to be injected into a patient for augmenting the amount of oxygen carried in the bloodstream; in so doing, these carriers are described as assisting normovolemic hemodilution and predonation. It appears that a benefit of these synthetic oxygen carriers is that end-points of blood sequestration could be greater than currently considered practicable. Hence, under proper conditions, patients may be able to tolerate greater volumes of sequestered blood since oxygen would be delivered not only by the red blood cells, but also by a perflubron emulsion as contemplated by Roth.

U.S. Pat. Nos. 5,074,838; 5,368,555; 5,318,511; and 4,623,518, are indicative of the art of extra corporeal circulation of the blood.

Notwithstanding these and related developments in the art, there appears to be no apparatus nor methodology which provides sufficiently safe and reliable conditions for autologous blood sequestration. Sequestration of blood prior to onset of a surgical procedure affords the most practicable methodology for reducing dependency upon allogeneic blood products. A methodology is needed wherein packed red blood cells and various coagulation factors may safely be removed from patients and then be recycled to the patient after surgery is completed. A practical, portable system that enables such effective application of acute normovolemic hemodilution is unknown in the art.

Furthermore, there is neither apparatus nor methodology that affords the advantage associated with keeping sequestered blood at 37° C. As will be understood by those skilled in the art, keeping blood substantially at this temperature optimizes the performance of platelets for clotting functions and the performance of leukocytes for mopping up bacteria contained in sequestered blood.

It is a disadvantage of the art that an anesthesiologist typically must contact a local blood bank to have specially constructed blood bags delivered to hospital operating rooms and the like, prior to surgical procedures. Commonly used sequestration procedures are slow and tedious, in which sequestered blood is maintained at room temperature, unfortunately, significantly below body temperature of 37° C. It will be appreciated by those skilled in the art that the introduction of 4 units of blood at room temperature into a patient's circulatory system could significantly reduce the patient's body temperature. This tendency is particularly germane in pediatric patients wherein heat loss occurs rapidly in the operating room environment, and, indeed, is associated with increased morbidity.

Furthermore, if blood products are not administered within 6 hours of being obtained, under A.A.B.B. rules, the blood must be refrigerated. But, the administration of cold packed red blood cells to pediatric patients has been associated with life-threatening arrhythmias. While blood warmers are, of course, available, they demand special apparatus and concomitant tubing, and, unfortunately, increase health care costs.

Thus, it is clear that there is presently no sequestration procedure which is inherently compatible with a patient's circulatory system with regard to blood flow and temperature, and which reliably forms a closed circuit therewith. Thus, it would be advantageous to utilize an apparatus which enables autologous blood sequestration via a closed circuit thereby assuring no interruption of a patient's innate circulatory system. Accordingly, these limitations and disadvantages of the prior art are overcome with the present invention, and improved means and techniques are provided which are useful for effectively and reliably sequestering a patient's own blood in a closed circuit arrangement that sustains the flow and temperature throughout the patient's circulatory system.

SUMMARY OF THE INVENTION

The present invention provides a simple apparatus and method for sequestering blood from a patient immediately prior to and during surgery, using a novel assembly of blood collection bags containing anticoagulant. The sequestered blood contained in this assembly of blood bags is kept in fluid contact with the patient throughout surgery, thereby assuring continuity with the patient's circulatory system and assuring blood sterility.

Thus, the present invention provides a closed circuit autologous blood sequestration reservoir system which is particularly effective prior to and during surgery. As will be appreciated by those skilled in the art, the present invention provides a methodology in which continuous flow is sustained between a novel blood bag assembly and a patient, commencing in the operating room immediately prior to surgery and, in some instances, even extending into the post-operative period. Accordingly, a method is provided for autologous sequestration of a patient's blood wherein such sequestration occurs without interrupting the continuous blood flow.

The present invention is preferably constructed with a plurality of oxygenated blood collection bags, preferably constructed from oxygen-permeable plastic and the like, which are interconnected with a corresponding plurality of valves which are interconnected with a plurality of flexible tubes which are, in turn, interconnected with a patient's right atrium. As will be appreciated by those skilled in the art, the plurality of tubes contemplated by the present invention may be interconnected with a peripheral artery.

According to the preferred embodiment of the present invention, a plurality of flexible tubes is interconnected with a patient's central venous system. More particularly, the preferred embodiment is interconnected with a patient's right atrium or large peripheral veins or peripheral artery for draining the patient's blood into a plurality of blood collection bags constructed from suitably plasticiser materials to enable sufficient oxygen to diffuse across the bags into the sequestered blood. As will be hereinafter described in detail, following the induction of anesthesia in the operating room, blood is sequestered into a collection bag assembly which forms a closed circuit blood reservoir system. The platelets contained within this sequestered blood benefit from aerobic oxidative metabolism, thereby assuring that such platelets function optimally as will be understood by those skilled in the art. The preferred embodiment further assures that the platelets of sequestered blood function optimally and have optimal longevity by providing agitation means to promote the diffusion of oxygen within the plurality of blood bags. As will be appreciated by those skilled in the art, after about 30–60 minutes of collecting blood into a virtual venous reservoir contemplated by the present invention, surgery immediately commences. As will become evident to those skilled in the art, this oxygenated blood, which is collected during surgery, trickles back into a patient's blood system, thereby emulating venous blood flow.

As will also be appreciated by those skilled in the art, blood sequestered according to the techniques taught by the present invention does not necessarily have to trickle back into a patient's blood system, but may remain stationary within the virtual venous reservoir. Furthermore, in selected cases, the blood sequestration methodology taught by the present invention may commence prior to the induction of anesthesia such as in the preoperative stage.

Another aspect of the present invention is to modify the procedure generally referred to as "normovolemic hemodilution" in the art to what may be considered to be a "hypovolemic hemodilution," wherein pumping means facilitates the return of sequestered blood to the patient via the closed circuit contemplated herein. As will be described in detail, this pumping means functioning as an auxiliary actuator also facilitates the flow of crystalloid simultaneously with the sequestration of blood.

Thus, the present invention provides an apparatus and method for transfusing blood that inherently minimizes risk to levels heretofore unknown in the art. The present invention also affords a closed circuit methodology for autologously collecting and circulating patients' blood which overcomes the objections of Jehovah's Witnesses to conventional blood transfusion procedures.

It is an object of the present invention to provide an apparatus and method for sustaining a closed circuit relationship between a patient and the patient's blood during a blood sequestration procedure.

It is another object of the present invention to provide an apparatus and method for controlling a patient's blood supply immediately before, during and immediately after surgery, wherein the patient's blood maintains continuous contact with the patient.

It is still another object of the present invention to provide a simple apparatus comprising a novel blood bag assembly which forms a closed circuit autologous sequestration reservoir system with a patient in preparation for, during and immediately after surgical procedures.

It is yet another object of the present invention to provide an apparatus and method which inherently avoids the risks of infection associated with allogeneic blood products.

It is another object of the present invention to provide an apparatus and method for avoiding the unsettled standards associated with allogeneic blood transfusion practices.

It is still another object of the present invention to provide a system for sequestering blood while avoiding all allogeneic blood products, thereby being acceptable to patients who have religious or health based objections to use of allogeneic blood.

It is yet another object of the present invention to provide a system for performing normovolemic hemodilution, pharmacologic vena-arterial compartmental translocation, hypovolemic hemodilution and modifications thereof, which is compatible with the religious beliefs of the Jehovah's Witnesses.

It is still another object of the present invention to provide a system for performing normovolemic hemodilution, pharmacologic vena-arterial compartmental translocation, hypovolemic hemodilution and modifications thereof, which is acceptable to patients and their families who are opposed to methods using allogeneic blood products.

It is a further object of the present invention to provide an apparatus and method which overcomes the disadvantages of intraoperative blood salvage.

It is another object of the present invention to provide an apparatus and method which overcomes the disadvantages of intraoperative blood salvage and autotransfusion thereof.

It is a further object of the present invention to provide an apparatus and method which overcomes the disadvantages of autologous predonation of blood.

It is another object of the present invention to provide an apparatus and method which economically and simply provides a warming environment for sequestered blood, thereby sustaining integrity and sterility of the sequestered blood.

It is still another object of the present invention to provide an apparatus and method which sustains the temperature of sequestered blood substantially at 37° C., thereby optimizing the performance of platelets for clotting functions and of leukocytes for mopping up bacteria during sequestration.

It is yet another object of the present invention to provide an apparatus and method for sequestrating blood into collection bags with an efficiency heretofore unknown in the art.

It is another object of the present invention to provide an apparatus and method for performing blood transfusions which sustains the collected blood temperature at normal body temperature.

It is another object of the present invention to provide an apparatus and method for sequestering blood which provides suitable agitation means for promoting optimal platelet functionality and longevity of the sequestered blood.

It is still another object of the present invention to provide a safe and reliable system for administering collected blood to a patient, after surgery, at varying rates of delivery.

It is yet another object of the present invention to provide a closed and uninterrupted system for sequestering blood into a plurality of collection bags from a patient and then for transfusing the sequestered blood to the patient.

It is still another object of the present invention to provide a closed and uninterrupted system for sequestering blood into collection bags from a patient and then for transfusing the sequestered blood to the patient, which inherently foregoes the normally recommended 6-hours' refrigeration requirements after blood sequestration.

It is still another object of the present invention to provide a closed and uninterrupted system for sequestering blood into oxygenated collection bags from a patient and then for transfusing the sequestered blood to the patient.

It is another object of the present invention to provide an apparatus and method for sequestering blood which provides actuator means for controlling the Hb content of the sequestered blood.

It is a specific object of the present invention to provide a closed circuit autologous blood sequestration reservoir system for sequestering blood from and cycling said sequestered blood to a patient disposed upon a table, prior to, during and after surgery, said system comprising: a plurality of oxygenated blood collection bags, configured to receive oxygen from an oxygen source, for sequestering blood from said patient; a valve assembly having a plurality of valves disposed medially between said plurality of oxygenated blood collection bags and said patient, for controlling cycling of said sequestered blood from and to said patient through a plurality of flexible tubing; each of said plurality of oxygenated blood collection bags configured with a plurality of receptacles disposed at one end thereof for sealably attaching to a tube of said plurality of flexible tubing; anticoagulant means stored within an anticoagulant container disposed proximal of said plurality of flexible tubing for preventing coagulation of said sequestered blood in said plurality of flexible tubing and in said plurality of oxygenated blood collection bags; each flexible tube of said plurality of flexible tubing interconnected with a corresponding valve of said plurality of valves of said valve assembly; flexible anticoagulant tubing interconnected with said anticoagulant container and a valve of said plurality of valves of said valve assembly for delivering said anticoagulant means into said plurality of oxygenated blood collection bags and said plurality of flexible tubing interconnected therewith; a flexible catheter tubing for interconnecting said valve assembly with said patient; a portable housing including a base portion having a longitudinal axis for receiving said plurality of oxygenated blood collection bags in said base portion and a shell portion pivotally attached to said base portion for covering said plurality of oxygenated blood collection bags in said base portion; said base portion further having a first longitudinal wall disposed at an end of said base portion where said shell portion is pivotally attached thereto, and further having a second longitudinal wall disposed at an end of said base portion opposite of said first longitudinal wall; said base portion further having warming means configured to abutably receive said plurality of oxygenated blood collection bags for maintaining said sequestered blood at a temperature of 37° C.; flow promoting means applied to said flexible catheter tubing for urging flow of said patient's blood from said flexible catheter tubing to said plurality of oxygenated blood collection bags.

It is another specific object of the present invention to provide a method for sequestering a patient's blood into a closed circuit autologous blood sequestration reservoir and for cycling said sequestered blood to said patient, prior to, during and after surgery, said method comprising the steps of: estimating a quantity of said patient's blood to be sequestered; attaching a flexible catheter tubing to said patient; priming with a first anticoagulant a plurality of flexible tubing interconnected with said flexible catheter tubing; further priming with said first anticoagulant a plurality of blood collection bags corresponding to and interconnected with said plurality of flexible tubing; force-feeding said patient's estimated blood into said flexible catheter tubing and then through said plurality of flexible tubing and then into said plurality of blood collection bags; controlling said flow of said sequestered blood through said plurality of flexible tubing into and from said plurality of blood collection bags; oxygenating said sequestered blood; agitating said sequestered blood contained in said plurality of blood collection bags; warming said sequestered blood to maintain a temperature of 37° C.; recycling said sequestered blood from said plurality of blood collection bags through said plurality of flexible tubing through said flexible catheter tubing into said patient; and retroflushing with a second anticoagulant said plurality of flexible tubing and said plurality of blood collection bags, for purging said sequestered blood from said plurality of flexible tubing and from said plurality of blood collection bags.

It is still another specific object of the present invention to provide a closed circuit autologous blood sequestration reservoir system for sequestering blood from and cycling said sequestered blood to a patient disposed upon a table, prior to, during and after surgery, said system comprising: a plurality of oxygenated blood collection bags for sequestering blood from said patient; a valve assembly having a plurality of valves disposed medially between said plurality of oxygenated blood collection bags and said patient, for controlling cycling of said sequestered blood from and to said patient through a plurality of flexible tubing; each of said plurality of oxygenated blood collection bags configured with a plurality of receptacles disposed at one end thereof for sealably attaching to a tube of said plurality of flexible tubing; anticoagulant means stored within an anticoagulant container disposed proximal of said plurality of flexible tubing for preventing coagulation of said sequestered blood in said plurality of flexible tubing and in said plurality of oxygenated blood collection bags; each flexible tube of said plurality of flexible tubing interconnected with a corresponding valve of said plurality of valves of said valve assembly; flexible anticoagulant tubing interconnected with said anticoagulant container and a valve of said plurality of valves of said valve assembly for delivering said anticoagulant means into said plurality of oxygenated blood collection bags and said plurality of flexible tubing interconnected therewith; a flexible catheter tubing for interconnecting said valve assembly with said patient; a portable housing including a base portion having a longitudinal axis for receiving said plurality of blood collection bags in said base portion and including a shell portion pivotally attached to said base portion for covering said plurality of oxygenated blood collection bags in said base portion; said base portion further having a first longitudinal wall disposed at an end of said base portion where said shell portion is pivotally attached thereto, and further having a second longitudinal wall disposed at an end of said base portion opposite of said first longitudinal wall; said base portion further having a plurality of parallel, spaced-apart channels disposed along said longitudinal axis of said base portion and configured for each channel of said plurality of channels to abutably receive one of said plurality of oxygenated blood collection bags; said base portion further having a plurality of slot means disposed in said second longitudinal wall of said base portion and also disposed contiguously of said plurality of channels, with each slot of said plurality of slots configured to receive a portion of a flexible tubing of said plurality of flexible tubing, with each of said portions of flexible tubing of said plurality of flexible tubing emanating from said plurality of oxygenated blood collection bags disposed in said plurality of channels; said base portion further including warming means interconnected with an external power source and configured to abutably receive said plurality of oxygenated blood collection bags for maintaining said sequestered blood at a temperature of 37° C.; and flow promoting means applied to said flexible catheter tubing for urging flow of said patient's blood from said flexible catheter tubing to said plurality of oxygenated blood collection bags.

These and other objects and features of the present invention will become apparent from the following detailed description, wherein reference is made to the figures in the accompanying drawings.

IN THE DRAWINGS

Figure 10A:
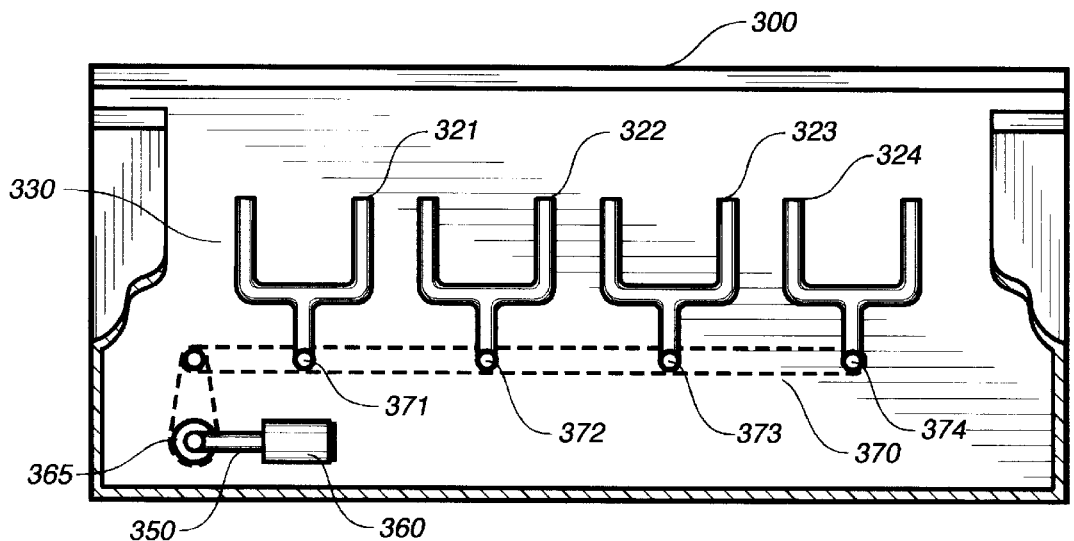
Figure 10B:
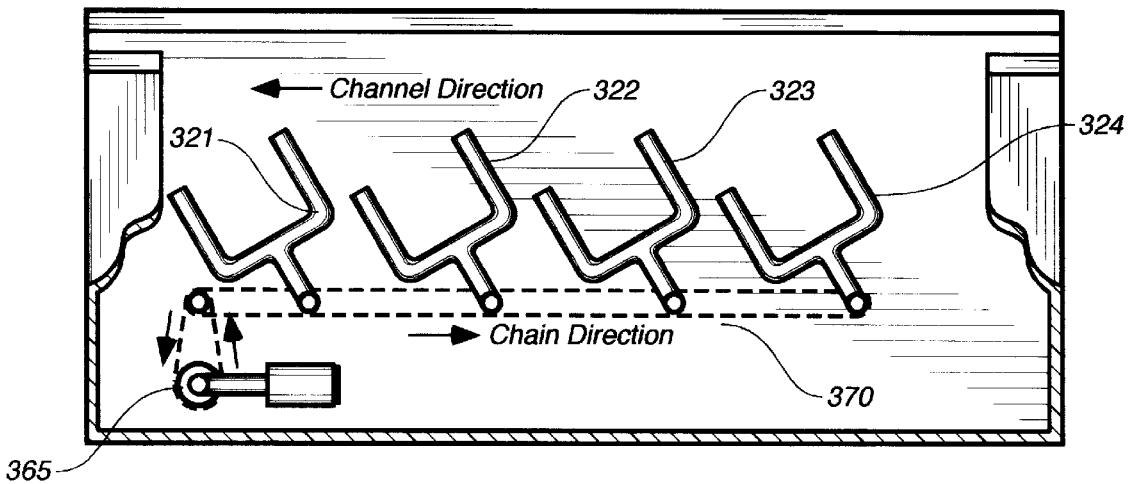

FIGS. 10A and B depict simplified frontal views showing an embodiment of the agitation means portion of the preferred embodiment of the present invention.

Figure 10C:
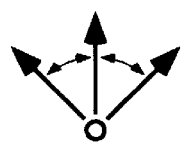

FIG. 10C depicts a simplified side view of the embodiment depicted in FIGS. 10A and B.

Figure 11A:
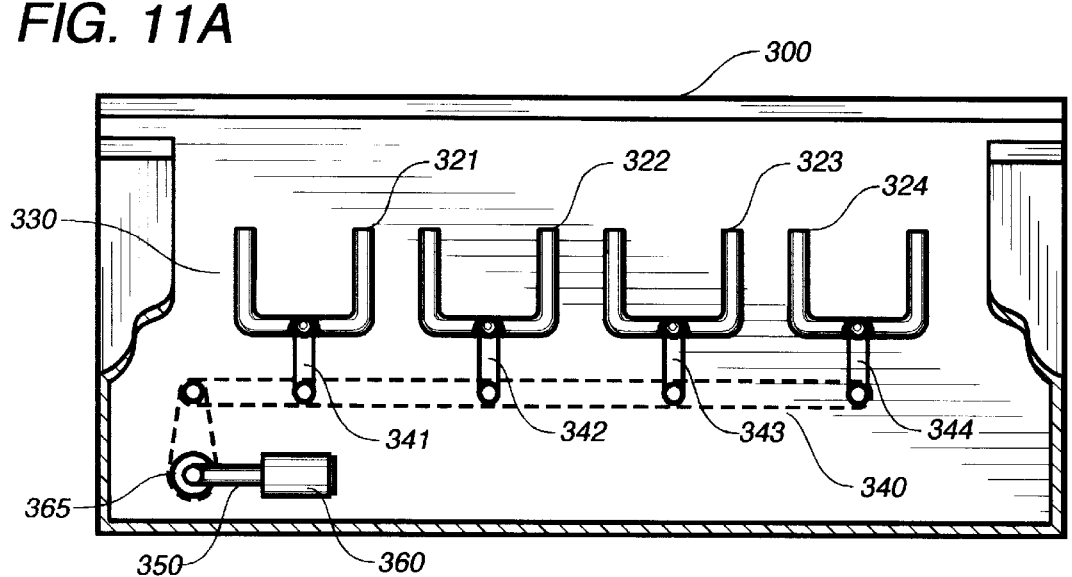
Figure 11B:
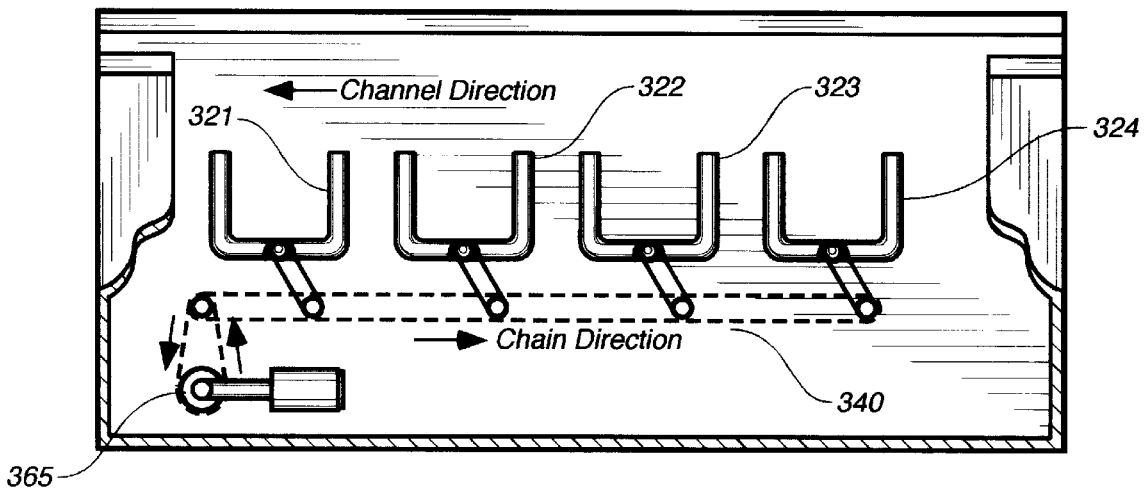

FIGS. 11A and B depict simplified frontal views showing an alternative embodiment of the agitation means portion depicted in FIGS. 10A and B.

Figure 11C:
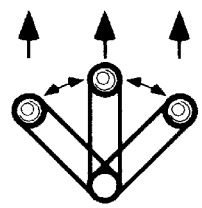

FIG. 11C depicts a simplified side view of the embodiment depicted in FIGS. 11A and B.

Figure 12:
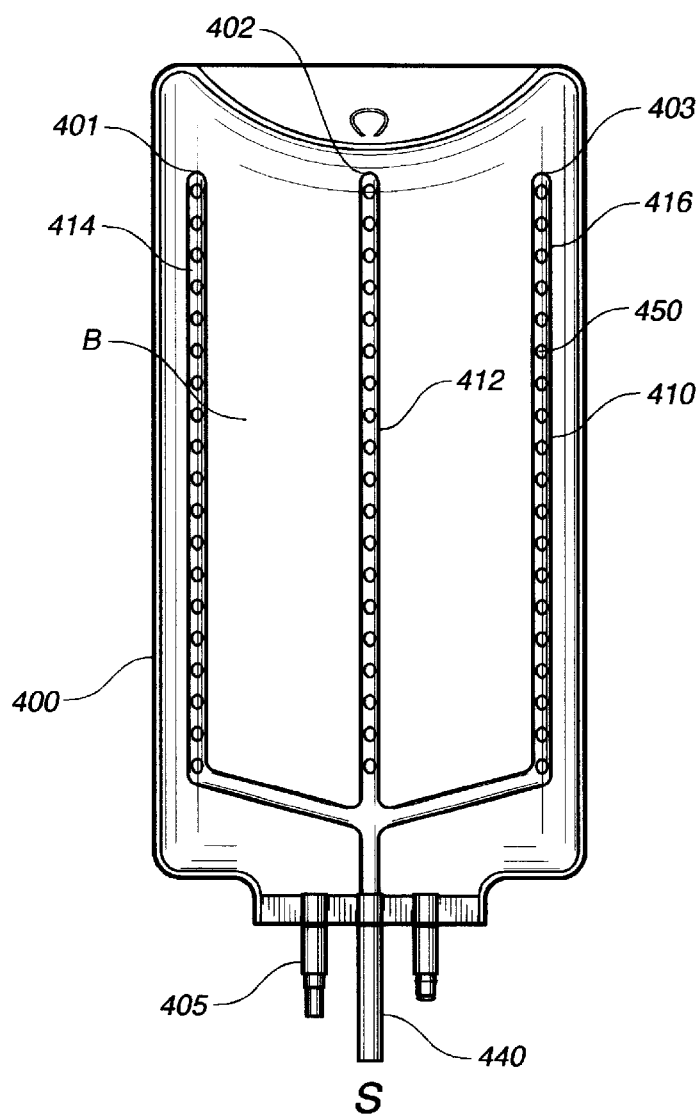

FIG. 12 depicts a simplified plan view showing an embodiment of the blood bag means embodying the present invention.

Figure 13:
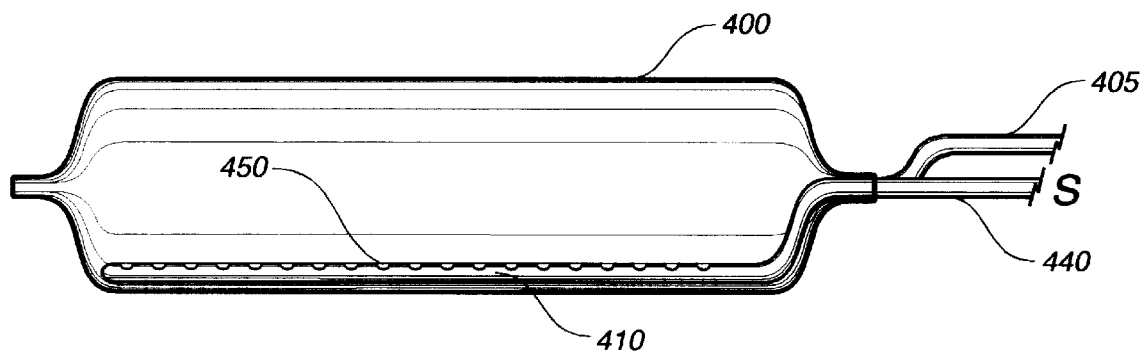

FIG. 13 depicts a side view of the embodiment of the blood bag means depicted in FIG. 12.

Figure 14:
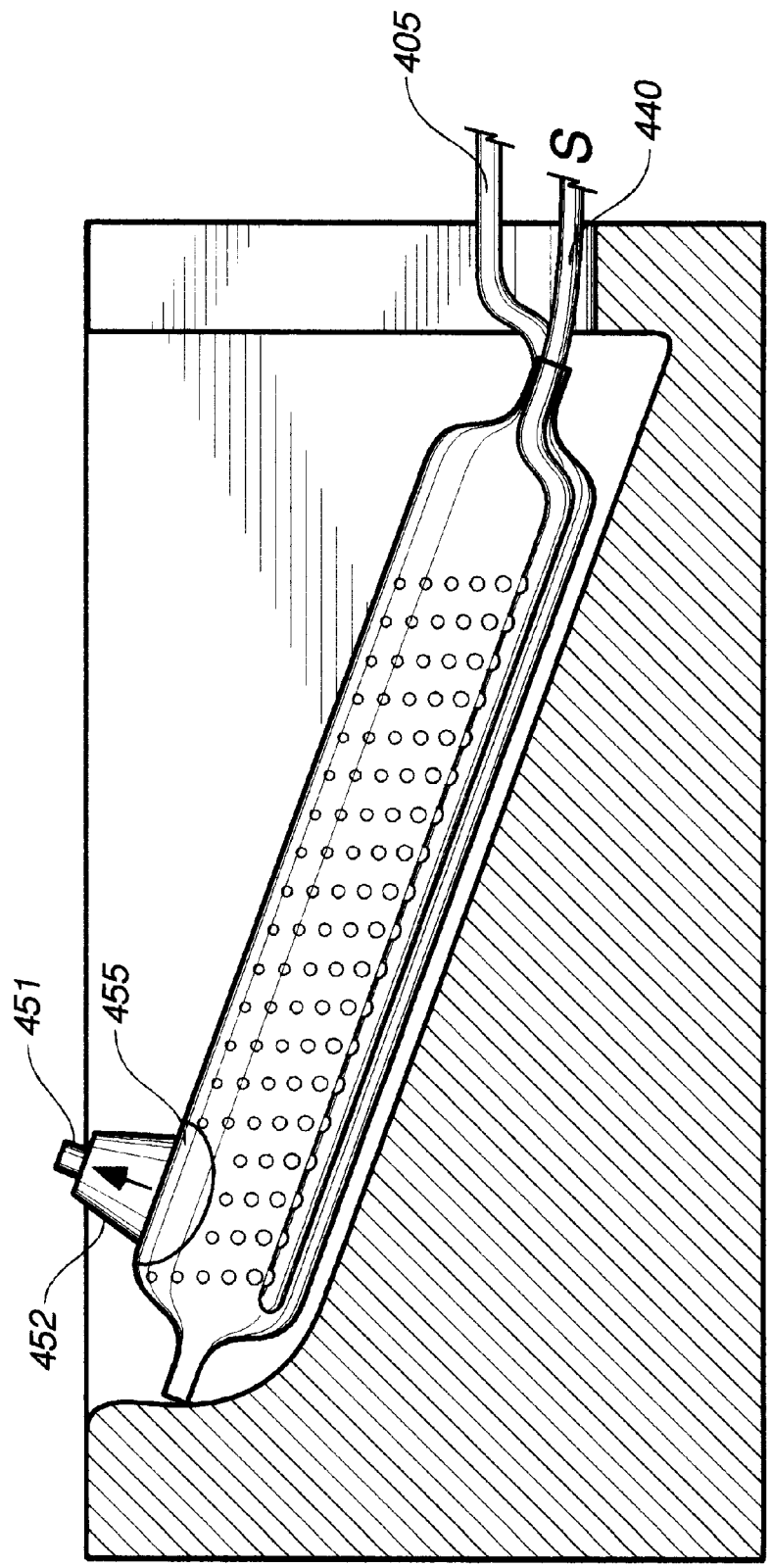

FIG. 14 depicts a simplified side view showing an alternative embodiment of the blood bag means embodying the present invention.

Figure 15:
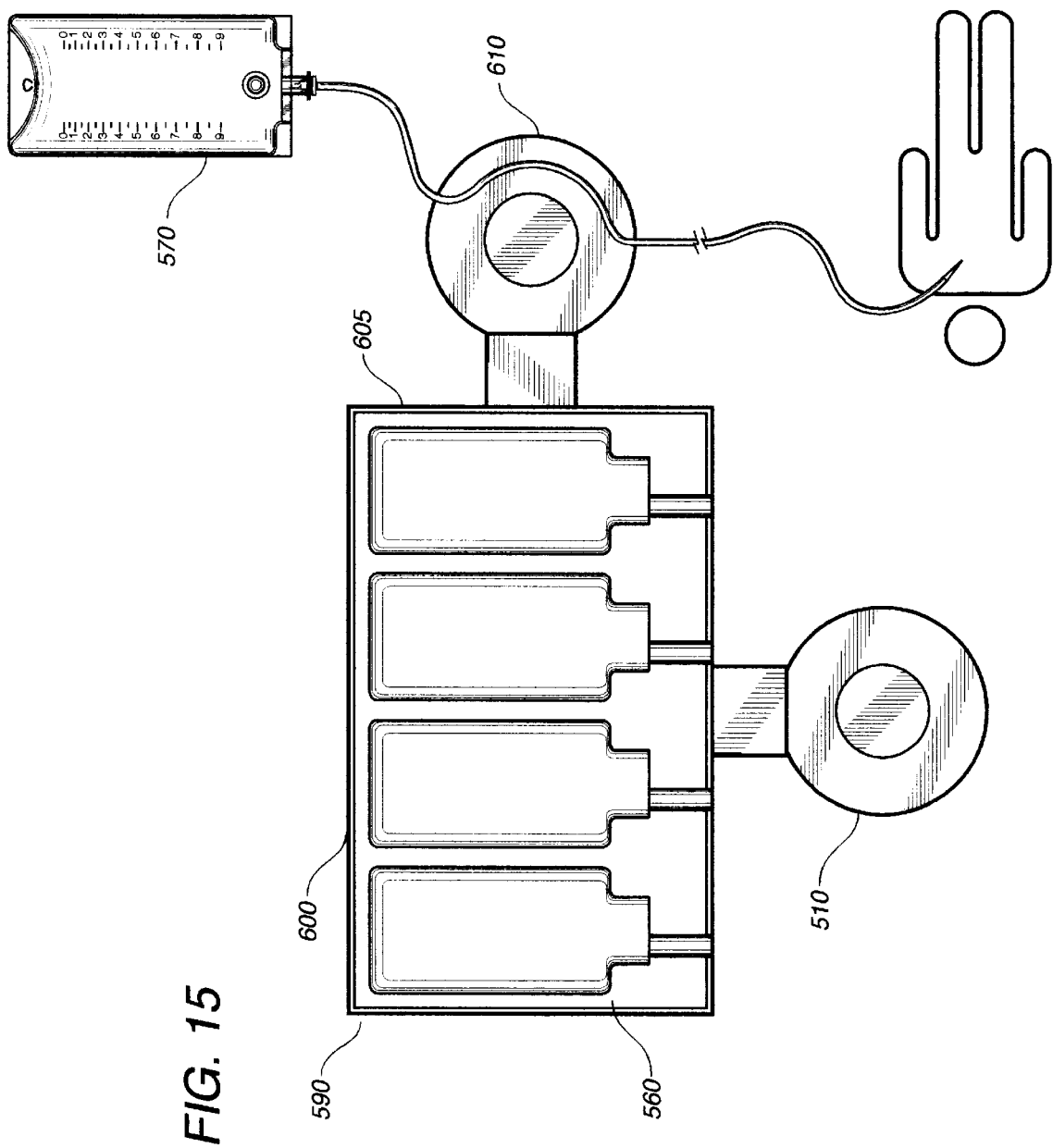

FIG. 15 depicts a simplified top plan view showing the preferred embodiment of the virtual venous reservoir taught by the present invention.

DETAILED DESCRIPTION

Figure 1:
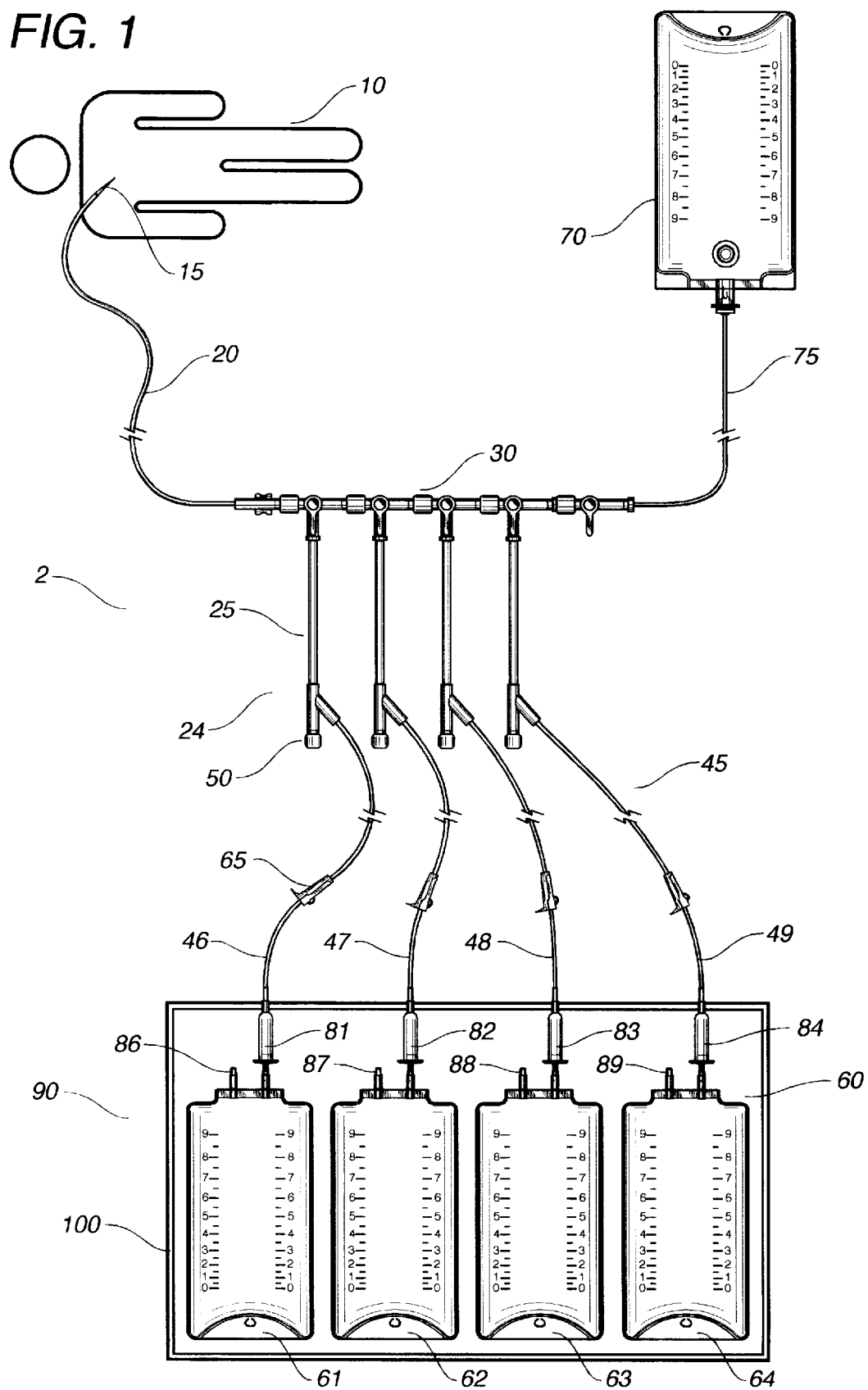
FIG. 1 depicts a simplified front view showing an embodiment of the present invention interconnected with a patient.

Now referring to FIG. 1, there is seen a simplified sketch of an embodiment of the present invention interconnected with a patient. More particularly, there is seen closed circuit virtual venous reservoir system 2 interconnected with patient 10. Flexible catheter tubing preferably comprising large bore flexible tubing 20 interconnected with catheter 15 is attached to preferably a central vein identified by numeral "V" located in the right atrium of patient 10. Alternatively, such a catheter tubing may be interconnected with one or more of a patient's peripheral veins or a peripheral artery to enable a sufficiently high rate of blood flow therealong. For example, tubing 20 preferably comprises tubing such as Model X36 high flow extension with inside diameter of 0.15 inches manufactured by Level 1 Technologies of Rockland, Mass. It will be appreciated by those skilled in the art that similar tubing having a larger inside diameter such as 0.18 inches could also be used, particular with an embodiment of the present invention using an actuator pump as will be hereinafter described in detail. Catheter 15 preferably comprises a multiple lumen catheter such as a large bore multi-lumen central venous catherization kit number AK-12123-H manufactured by Arrow International of Reading, Penn. or Mahurkar Bi-Cath CVC tray number 499221 manufactured by Maxim Medical Products of Athens, Tex. As will become clear to those skilled in the art, a multi-lumen catheter 15 contemplated under the present invention typically is constructed with 2–3 separate tubular channels contained with the tubular catheter. Each such separate channel should preferably have a gauge of 12, 14 or 16, contained within a total catheter tubing of 8–12 French. It will be understood that respective tubing 20 and catheter 15 should be selected to provide a sufficient internal diameter to promote blood flow in the range of 25 ml/min to 175 ml/min.

As is also understood by those skilled in the art, catheters are usually measured in units of French corresponding to the circumference measured in mm. Lumens contained in multi-lumen catheters, on the other hand, are typically measured by gauge corresponding to the number of items that may be situated side by side within an inch. Tubing, on the other hand, is typically identified by its internal diameter measured in inches.

Referring to FIGS. 1–4, tubing 20 is interconnected with valve assembly 30 which controls the cycling of blood through tubing assembly 24 into virtual venous reservoir 90 having plurality of blood collection bags 60 contained within housing 100. Valve assembly 30 also controls the flow of either crystalloid or saline from anticoagulant bag 70 to plurality of blood collection bags 60. Tubing assembly 24 comprises plurality of tubing segments or truncated tubing members 25, corresponding plurality of couplings 50, corresponding plurality of tubing members 45 and plurality of clamps 65 attached to plurality of tubing members 45. Plurality of blood collection bags 60 comprises blood collection bags 61, 62, 63 and 64. Anticoagulant fluid bag 70 feeds anticoagulant into valve assembly 30 through conventional intravenous tubing 75. As should be evident to those skilled in the art, anticoagulant fluid contemplated by the present invention typically comprises citrate dextrose for priming or normal saline solution for retroflushing, as will be hereinafter described in detail.

Figure 2:
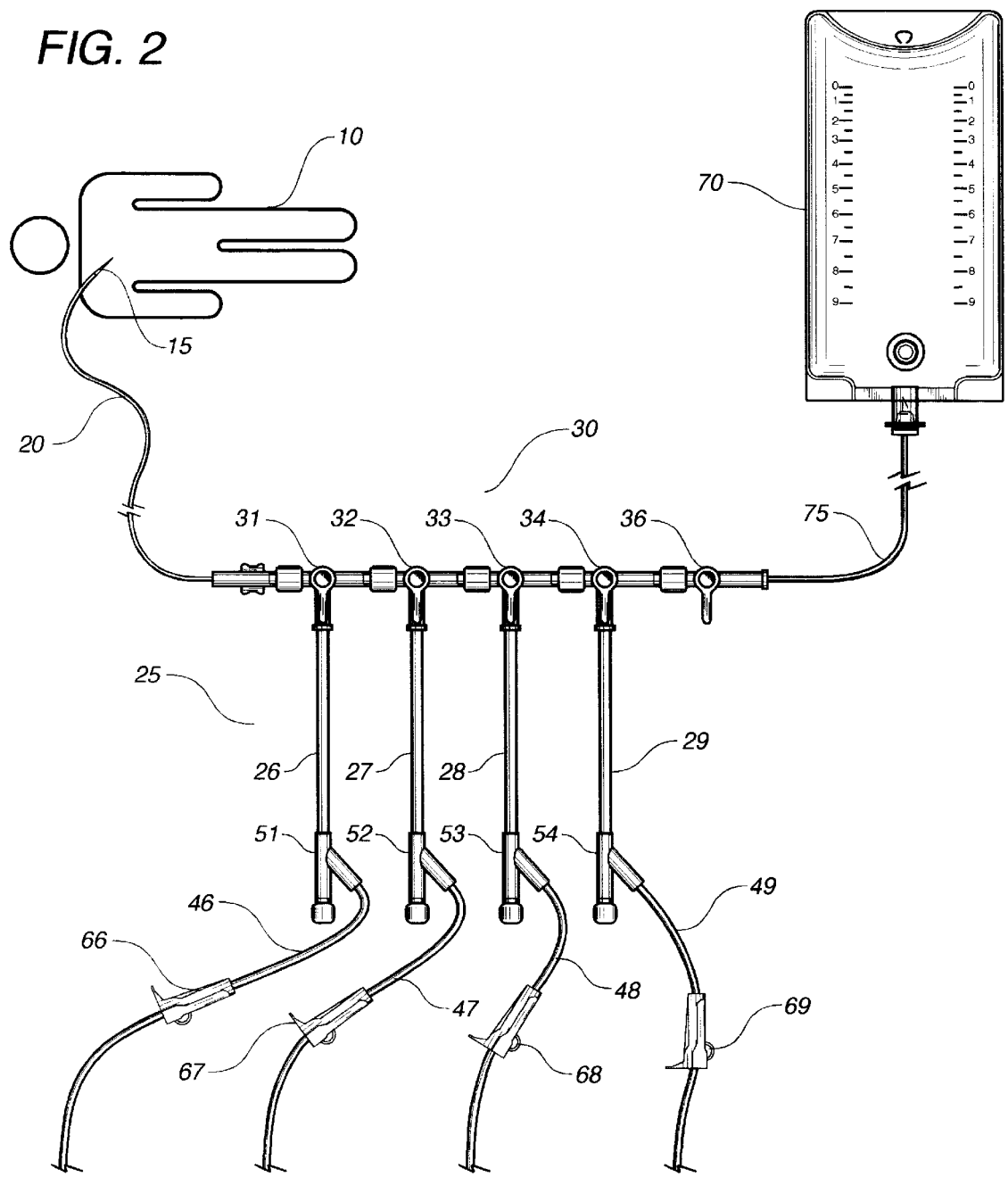
FIG. 2 depicts a front view of a portion of an embodiment of the present invention depicted in FIG. 1.
Figure 3:
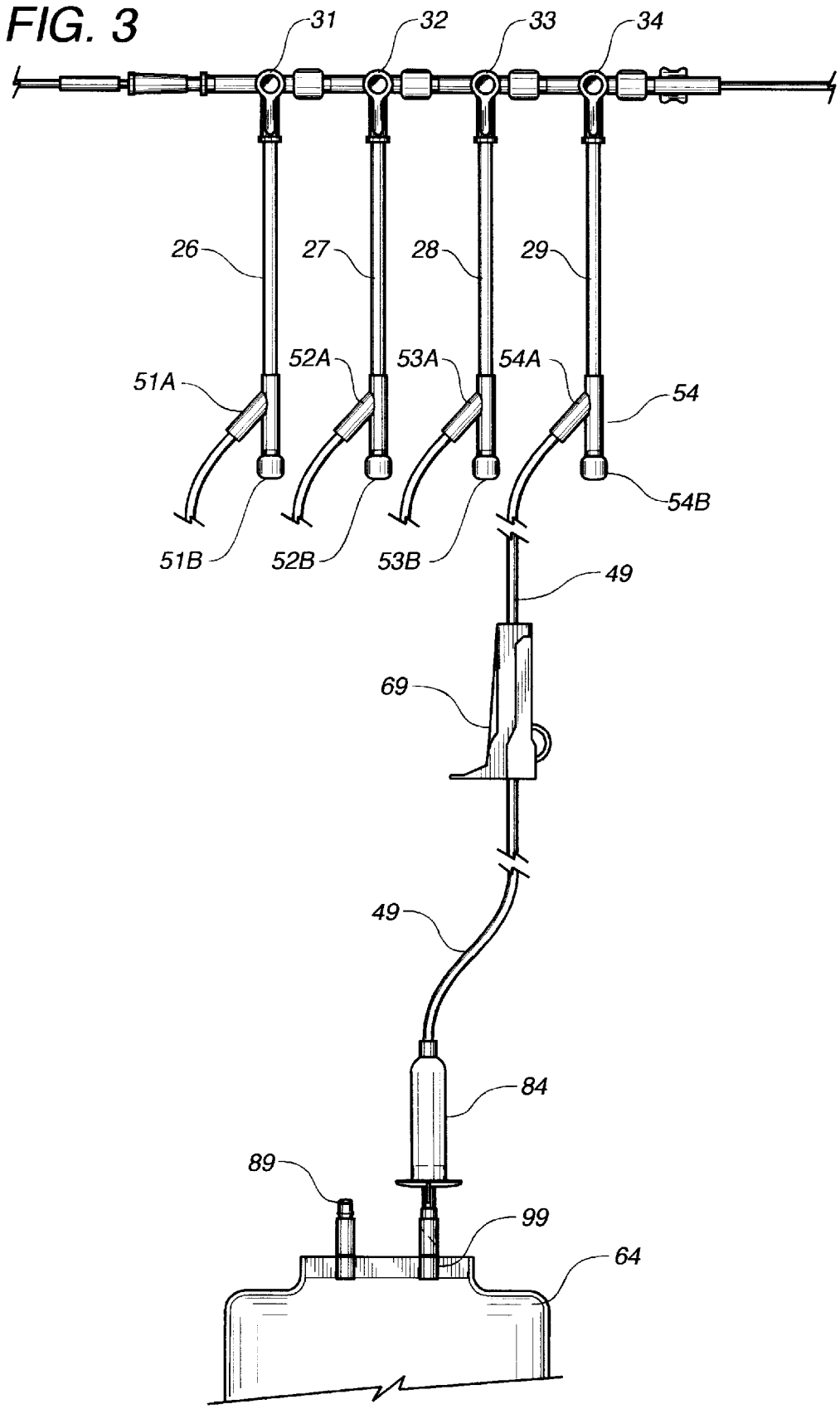
FIG. 3 depicts a front view of another portion of an embodiment of the present invention depicted in FIG. 1.

It is clearly seen that valve assembly 30 comprising plurality of valves 31, 32, 33, 34 and 36 is interposed between flexible tubing 20 and 75. Each of valves 31, 32, 33, 34 and 36 preferably comprises a conventional stopcock or any other suitable device enabling liquid flow in various directions. As depicted in FIGS. 1–3, valves 31, 32, 33 and 34 are interconnected with corresponding like-sized plurality of tubing segments 45. More particularly, valve 31 is interconnected with tubing segment 26, valve 32 is interconnected with tubing segment 27, valve 33 is interconnected with tubing segment 28, and valve 34 is interconnected with tubing segment 29. It has been found that stopcocks such as large bore "Hi-Flo" stopcock model number W20058 manufactured by Walrus of Woburn, Mass. provides the intended flow control of each of these valves.

Plurality of tubing segments 25 is interconnected with corresponding plurality of couplings or fittings 50 which are, in turn, interconnected with corresponding plurality of tubing 45. In particular, tubing segment 26 is interconnected with coupling 51, tubing segment 27 is interconnected with coupling 52, tubing 28 is interconnected with coupling 53, and tubing segment 29 is interconnected with coupling 54.

As depicted in FIG. 3, each coupling of plurality of couplings 50 preferably has two ports: one port (identified by numeral "A") for connection with a corresponding flexible tube of plurality of flexible tubes 45 attached to a blood collection bag of plurality of blood collection bags 60, and the other port (identified by numeral "B") for enabling local means for injection of medication or for providing secondary flushing ability as will be hereinafter described. Thus, port 51A of coupling 51 interconnects tubing segment 26 with flexible tubing 46. Similarly, port 52A of coupling 52 interconnects tubing segment 27 with flexible tubing 47; port 53A of coupling 53 interconnects tubing segment 28 with flexible tubing 48; and port 54A of coupling 54 interconnects tubing segment 29 with flexible tubing 49. Also included in valve assembly 30 is valve 36 which is interconnected with tubing 75 which is attached to anticoagulant fluid bag 70.

Referring now to FIGS. 1–3, plurality of clamps 65 is attached to plurality of tubing 45 which is attached to corresponding plurality of couplings 50. Thus, clamp 66 is attached to flexible tubing 46, clamp 67 is attached to flexible tubing 47, clamp 68 is attached to flexible tubing 48, and clamp 69 is attached to flexible tubing 49. FIG. 3 more particularly depicts the preferred embodiment of clamp 69 indicative of the other clamps comprising plurality of clamps 65. A typical clamp suitable for controlling the rate of flow of either blood or retroflush through the various tubing described herein is called a "CAIR" clamp by Abbott Laboratories of Chicago. As an acronym for "constant accurate infusion rate," CAIR clamp 66 provides a convenient and reliable means for adjusting flow rate through tubing 48.

Now referring to FIGS. 1–3, there is depicted blood bag assembly 60 comprising plurality of blood collection bags 61, 62, 63 and 64. Each of blood bags 61, 62, 63 and 64 is interconnected with flexible tubing 46, 47,48 and 49, respectively. As is well known in the art, a blood collection bag may be constructed with an integrated tube such as tube 46 attached to collection bag 61. Alternatively, a blood collection bag may be constructed with a receptacle for sealably receiving a sharp pointed end of a tube wherein blood is sealably transported from and to the bag through the tube. Accordingly, the remote ends of tubes 46, 47, 48 and 49, located adjacent blood collection bags 61, 62, 63 and 64, respectively, may include a plurality of introducers which sealably secure these tubes to the corresponding collection bag. Such an arrangement, of course, enables blood to be sequestered and cycled back to the patient without any leakage thereof.

Thus, there is depicted in FIG. 3 introducer 99 attached on one end sealably to corresponding collection bag 64, respectively, and the other opposite end to drip chamber 84. As will be appreciated by those skilled in the art, it is advantageous to include at the distal end of plurality of tubing 25 a plurality of drip chambers so that the rate of blood sequestered into plurality of collection 60 or the flow of sequestered blood from the collection bags may be readily observed. Accordingly, depicted in FIG. 1 is drip chamber 81 attached to tubing 46, drip chamber 82 attached to tubing 47, drip chamber 83 attached to tubing 48, and drip chamber 84 attached to tubing 49. Also depicted is a plurality of injection ports, comprising port 86 affixed to blood bag 61, port 87 affixed to blood bag 62, port 88 affixed to blood bag 63, and port 89 affixed to blood bag 64, respectively, for injection of medication into the sequestered blood or for supplemental flushing of the bags once the sequestered blood has been cycled back to the patient.

As will be understood by those skilled in the art, the use of anticoagulant is advantageous for sustaining uninterrupted fluid communication between a patient's circulatory system and the blood sequestration system taught herein. Preferably, an anticoagulant such as a citrate dextrose formulation manufactured by Fenwal Division of Baxter Healthcare Corporation of Deerfield, Ill., is used. After blood sequestration, normal saline is used to retroflush tubing assembly 24 to prevent coagulation of blood therein.

Figure 9A:
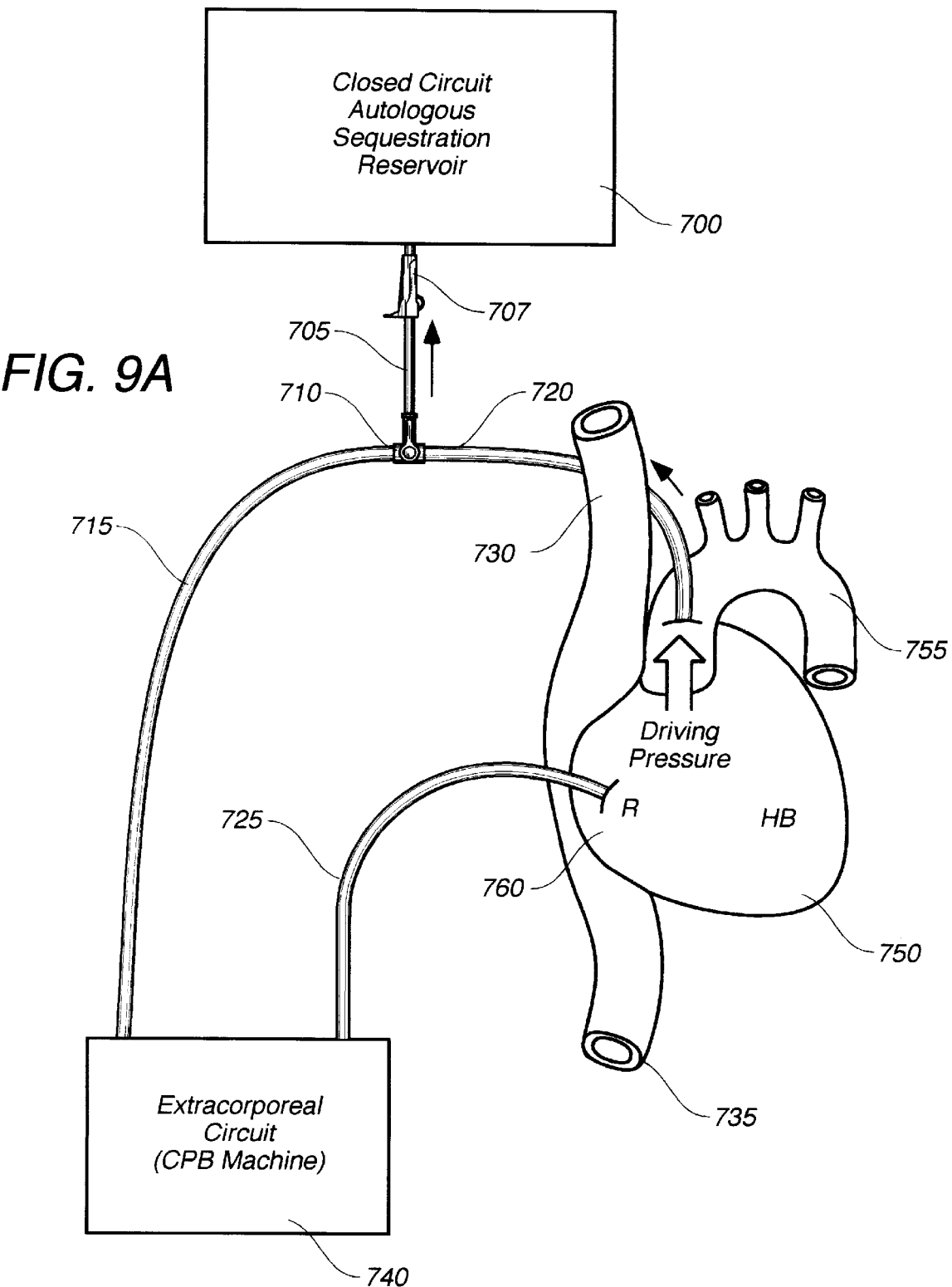
FIG. 9A depicts a simplified frontal perspective view of an embodiment of the present invention applicable for a heparin-based surgical procedure commonly performed in the art.

A common approach used by those skilled in the art is to anticoagulate patients with a drug called "heparin" preparatory to performing a cardiopulmonary bypass during cardiac surgery. Such a heparinized patient could then be interconnected with embodiments of the closed circuit autologous sequestration reservoir taught by the present invention. As examples, as shown in FIGS. 9A and B, in anticipation of a cardiopulmonary bypass, a plurality of cannula means are appropriately situated in the exposed heart 750 of a patient to be interconnected with cardiopulmonary bypass apparatus (abbreviated "CPB") 740, i.e., "heart-lung machine," well known in the art to such patient with embodiment of closed circuit autologous sequestration reservoir 700. In particular, large venous cannula means 725 is placed in a patient's right atrium ("R") 760 and interconnected with CPB 740. Similarly, large arterial cannula means 720 is place in aorta 755 and interconnected with CPB 740 through extracorporeal tubing connector means 710 which is placed in arterial line 715. Thus, arterial tubing line 715 and tubing 705 leading into closed circuit autologous sequestration reservoir 700 are interconnected by extracorporeal tubing connector means 710. As will be understood by those skilled in the art, heparinized blood HB may be rapidly sequestered from heart 750 into autologous sequestration reservoir 700 via a typical aortic driving pressure of 120 mm Hg. The arrow shown in FIGS. 9A and B depicts the direction of blood sequestered from a patient's heart 750 through aorta 755 and, in turn, passing through arterial cannula means 720 interconnected with tubing 705 at extracorporeal tubing connector means 710.

Figure 9B:
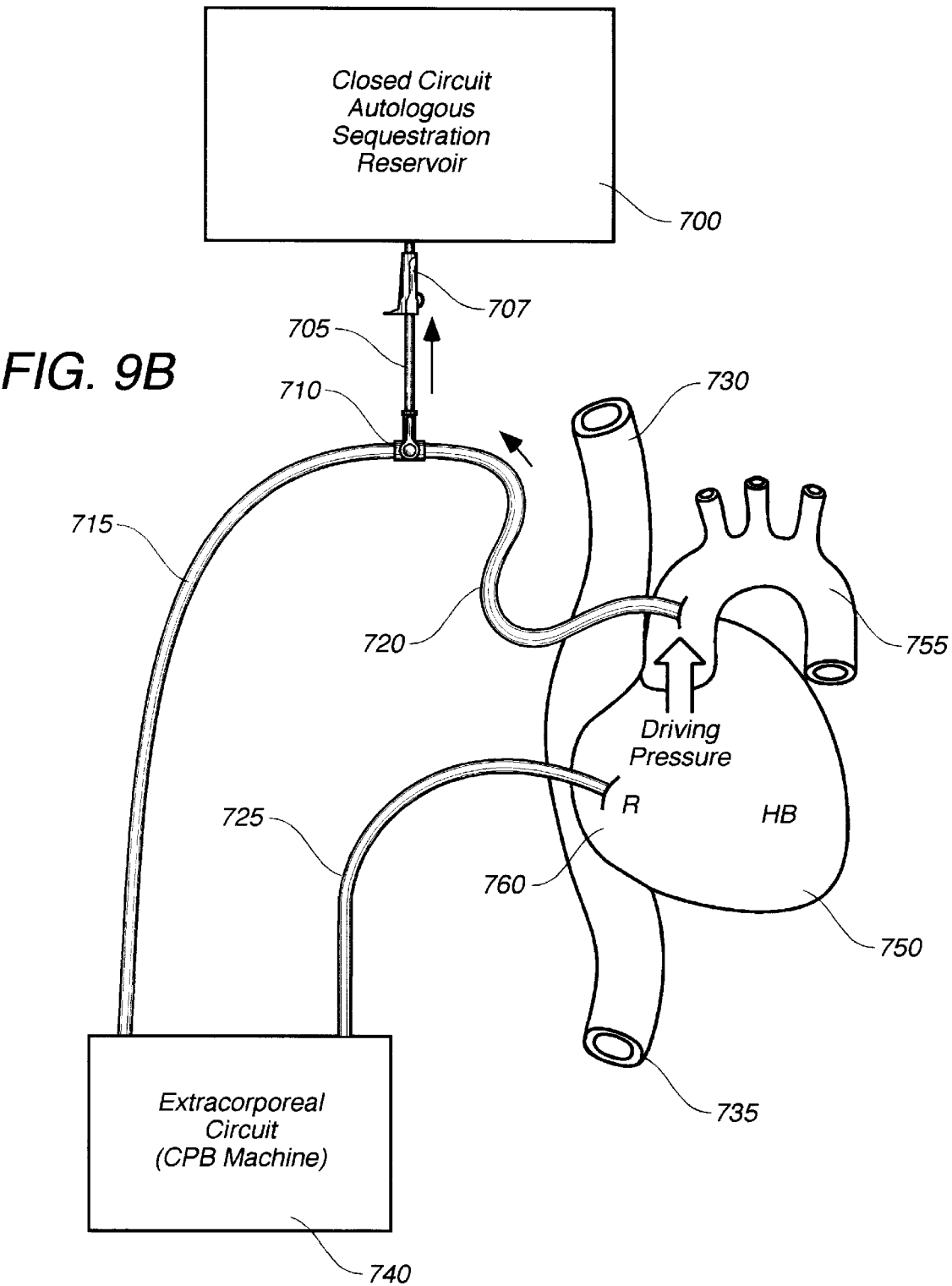
FIG. 9B depicts a simplified frontal perspective view of a variation of the embodiment of the present invention depicted in FIG. 9A for a heparin-based surgical procedure commonly performed in the art.

As will be evident to those skilled in the art, FIG. 9A depicts tubing 720 entering through the top portion of aorta 755 behind superior vena cava 730, while FIG. 9B depicts tubing 720 entering through a side portion of aorta 755 in front of superior vena cava 730. Tubing 725 represents the venous return from CPB 740 to right atrium 760. Also depicted is clamp means 707 disposed upstream of extracorporeal tubing connector means 710 which is preferable for regulating the driving pressure from heart 750. It has been found that Straight/Luer connectors, e.g., model numbers EC-2155 and EC-2165, from Gish Biomedical, Inc. of Irvine, Calif. provide the performance contemplated by the present invention. Thus, satisfactory performance of embodiments of the present invention depicted in FIGS. 9A and B are obtained wherein the diameters of tubing means 715 and 720 are approximately ¼ inch and the diameter of tubing means 705 is approximately ⅛ inch.

If this rapid sequestration is associated with any hemodynamic changes, as will be understood by those skilled in the art, the cardiac surgery should preferably commence without delay in order to support the patient's blood circulation. Once surgery starts, however, further sequestration is limited because of the additional hemodilution produced by the extra corporeal circuit manifest by the cardiopulmonary bypass apparatus CPB. Since the patient has already been heparinized, an embodiment of the instant autologous reservoir system without anticoagulant as hereinbefore described would be used. As will be hereinafter described, use of an actuator pump may be advantageous depending upon a patient's aortic pressure.

As will be appreciated by those skilled in the art, this embodiment of the present invention teaches an approach to sequestration which corresponds to post-heparinization rapid blood sequestration. Not only is this novel sequestration methodology quick and straightforward, but also provides benefits associated with the inherent security of the well-established cardiopulmonary bypass procedure, particularly under circumstances in which a patient cannot tolerate rapid blood sequestration. There is, of course, a risk factor: such rapid blood sequestration may be unsafe for some patients, subjecting them to greater hemodynamic instability and to possible inadequate perfusion of the heart, brain, and kidneys. As will be appreciated by those conversant with the art, however, such risk is mitigated by using a system based upon a closed circuit sequestration and which sustains optimal blood temperature as taught by the present invention.

This risk factor, fortunately, is addressed by the present invention, wherein a closed circuit featuring an autologous sequestration reservoir is used. As achieved by the present invention, sustaining sequestered blood at or near normal body temperature inherently preserves the function and integrity of cellular elements, including leukocytes, red blood cells and platelets. As will be evident to those skilled in the art, preservation of normal blood function is the foundation of successful sequestration. Furthermore, sustaining a closed circuit blood collection system as is taught herein is inherently maximally sterile since asepsis is assured. Additionally, providing an embodiment of a closed-circuit autologous sequestration reservoir system is important for people and religious denominations who are opposed to any interruption of the continuity of a blood circuit-based system, i.e. Jehovah's Witnesses.

As will be appreciated by those skilled in the art, heparin has effects on platelets that may be regarded as being fundamentally noxious. Heparin produces a state of "platelet activation" in which platelets aggregate or clump, and may degranulate to release substances including ADP, PF4, etc., referred to as a "platelet release reaction." Interesting, once activated, platelets may disaggregate, but thereafter the ability to respond to stimuli appears to be permanently blunted or refractory. Rapidly sequestered blood as hereinbefore described is apt to contain activated platelets which might lose some of their procoagulant function when later transfused back into a patient. Under these circumstances, of course, an important benefit of sequestration as contemplated by the present invention, i.e. preservation of optimal platelet function, might be permanently impaired or even completely lost.

Although the post-heparinization rapid sequestration technique hereinbefore described affords ease-of-use and convenience advantages to surgeons performing cardiac procedures, it is not a preferable implementation of the present invention because of known noxious effects of heparin upon platelets and the risk of hemodynamic instability. There are even other complications associated with heparin administration that further impact platelets, including heparin-induced transient or reversible thrombocytopenia, and heparin induced thrombocytopenia. While these phenomena are reported to be rare, there is nevertheless a sufficient basis for exploiting the various inherent advantages associated with the instant sequestration methodology wherein whole blood uses anticoagulant means other than heparin.

Since platelet function may be optimized by providing an environment that assures aerobic oxidative metabolism, it has been found that such an environment may be achieved by using blood collection bags which are constructed with suitable plasticizers to promote oxygen diffusion across the outer surface of the bags into the sequestered blood. Accordingly, the preferred embodiment of the present invention contemplates using such oxygenated blood collection bags. Representative commercially available plastic bags which are suited for this purpose include Fenwal PL-1240, Cutter CLX which correspond to PVC with a trimellitate, non-DEHP plasticizer such as TOTM; Fenwal PL-732 which corresponds to blow-molded polyolefin; Terumo XT-612 which corresponds to thin-film PVC with a 2-DEHP plasticizer; and Fenwal PL-2209 which corresponds to PVC with citrate based non-DEHP plasticizer.

Under the present invention it is contemplated that a collection bag preferably comprises a one-liter plastic bag having an entry point to sealably receive an introducer as hereinbefore described. Of course, instead of using a plurality of introducers having sharp ends inserted into the entry port of each of a plurality of blood collection bags, it is also within the teachings of the present invention to provide an integrated arrangement of blood collection bags in which tubing is constructed to be already inserted therein, thereby negating the introducer function.

Referring again to FIGS. 1–3, as will be appreciated by those skilled in the art, the retroflush procedure as contemplated herein comprises flushing tubing assembly 24 wherein each of flexible tubing segments 26, 27, 28 and 29; couplings 51, 52, 53 and 54; and flexible tubing 46, 47, 48 and 49 preferably with normal saline solution, subsequent to blood sequestration as disclosed herein. Such retroflushing, of course, prevents coagulation of blood within this network of tubing. Thus, according to the present invention, subsequent to sequestration of blood into plurality of collection bags 60, by regulating the flow from bag 70 containing normal saline solution (which replaced the bag containing citrate anticoagulant and the like), blood should preferably be purged from tubing assembly 24 as will be described herein.

Subsequent to the sequestration of blood into collection bag 61, valve 36 is placed into an open position to enable flow of saline crystalloid through tubing 75 then through valve 36 to valve 31. Valve 31, in turn, is opened to enable flow of this crystalloid through tubing segment 26 through coupling 51 through tubing 46 and into blood collection bag 61. When both tubing 75 and 26 are clear of blood, i.e., by visually observing through this transparent/translucent tubing, indicating that retroflush has been completed, valve 31 is closed to prevent any further fluid flow through tubing 26. This procedure is repeated for valves 32, 33 and 34, in turn, wherein crystalloid flows through corresponding tubing segments 27, 28 and 29 then through corresponding couplings 52, 53 and 54 and then through tubing 47, 48 and 49 and into corresponding blood collection bags 62, 63 and 64. When tubing assembly 24 is clear of blood, all of the hereinbefore stopcocks comprising valve assembly 30 are closed to prevent any further flow of saline solution therethrough.

It should be understood by those skilled in the art that the present invention also contemplates, instead of using anticoagulant delivered from a reservoir bag 70 as hereinbefore described, using tubing manufactured with an inner surface coating of anticoagulant. Using this embodiment of the present invention, when flowing blood contacts the coated inner tubing surfaces, coagulation is prevented or at least inhibited. Since coagulation is inherently minimized using this embodiment, the need for the hereinbefore described retroflushing procedure is likewise minimized.

Figure 4:
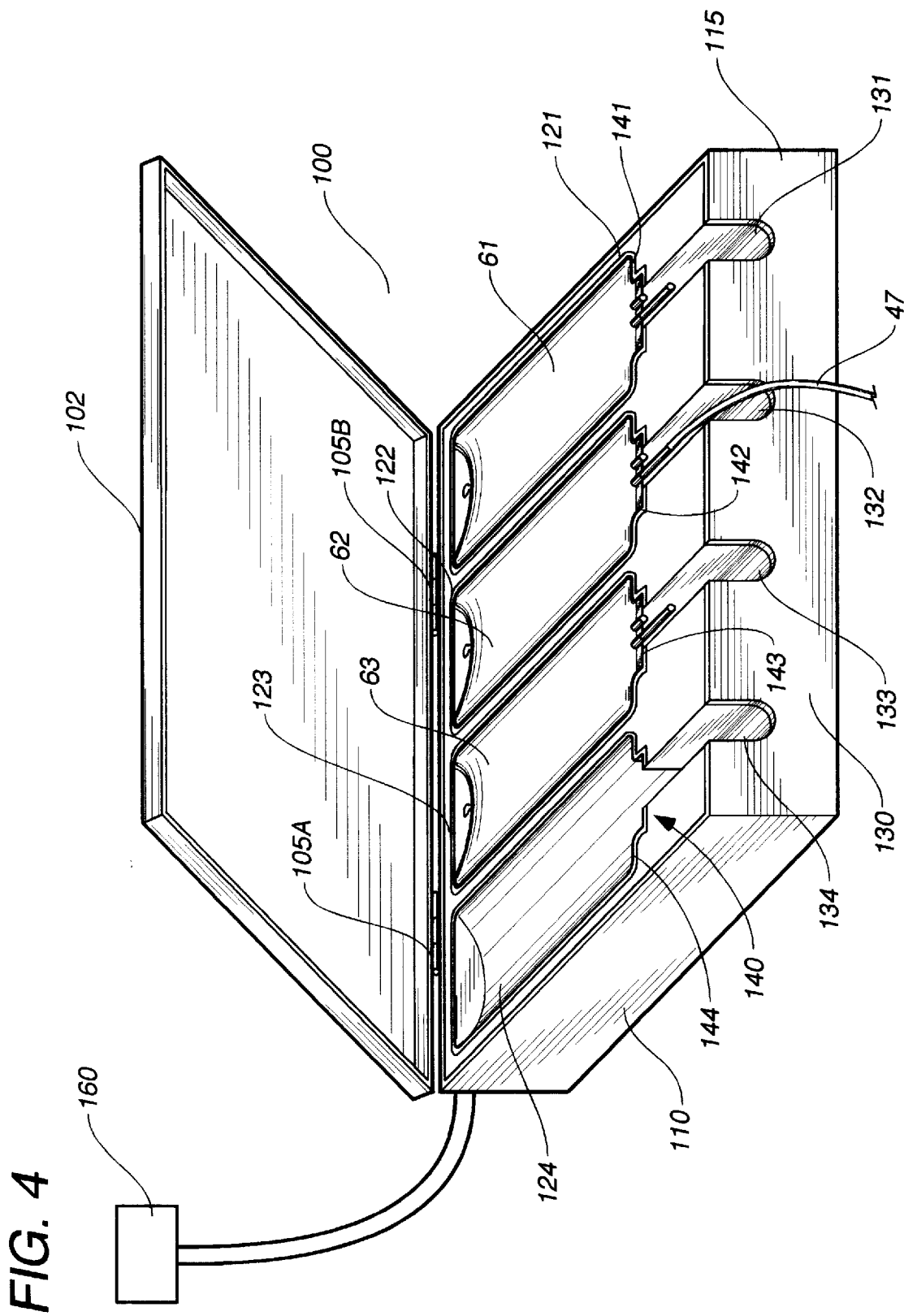
FIG. 4 depicts a simplified frontal perspective view of a portion of an embodiment of the present invention.

As shown in FIG. 4, the virtual venous reservoir system taught by the present invention includes housing 100 for preferably containing plurality of blood collection bags 60, comprising collection bags 61, 62, 63 and 64. Each of these blood collection bags is received by corresponding plurality of preferably rectangular plates or channels 120 which securably position the bags transversely of the longitudinal axis of the housing. Housing 100 comprises base portion 110 and cover portion 102. Cover portion 102 is preferably pivotally attached to base portion 110 with hinges 105A and B.

Under the present invention, cover portion 102 is preferably snugly received by base portion 110 without imparting any undue pressure upon plurality of blood collection bags 60. As will be appreciated by those skilled in the art, such pressure upon any of blood collection bags 61, 62, 63 or 64 could damage elements of the sequestered blood. It should be clear that cover portion 102 should fit snugly upon base portion 110 to promote a substantially adiabatic environment for the sequestered blood. According to the preferred embodiment of the present invention, closing lid 102 upon base 110 preferably activates a switch (not shown) which causes heat to be applied to plurality of plates 120 as will be hereinafter described.

Figure 7:
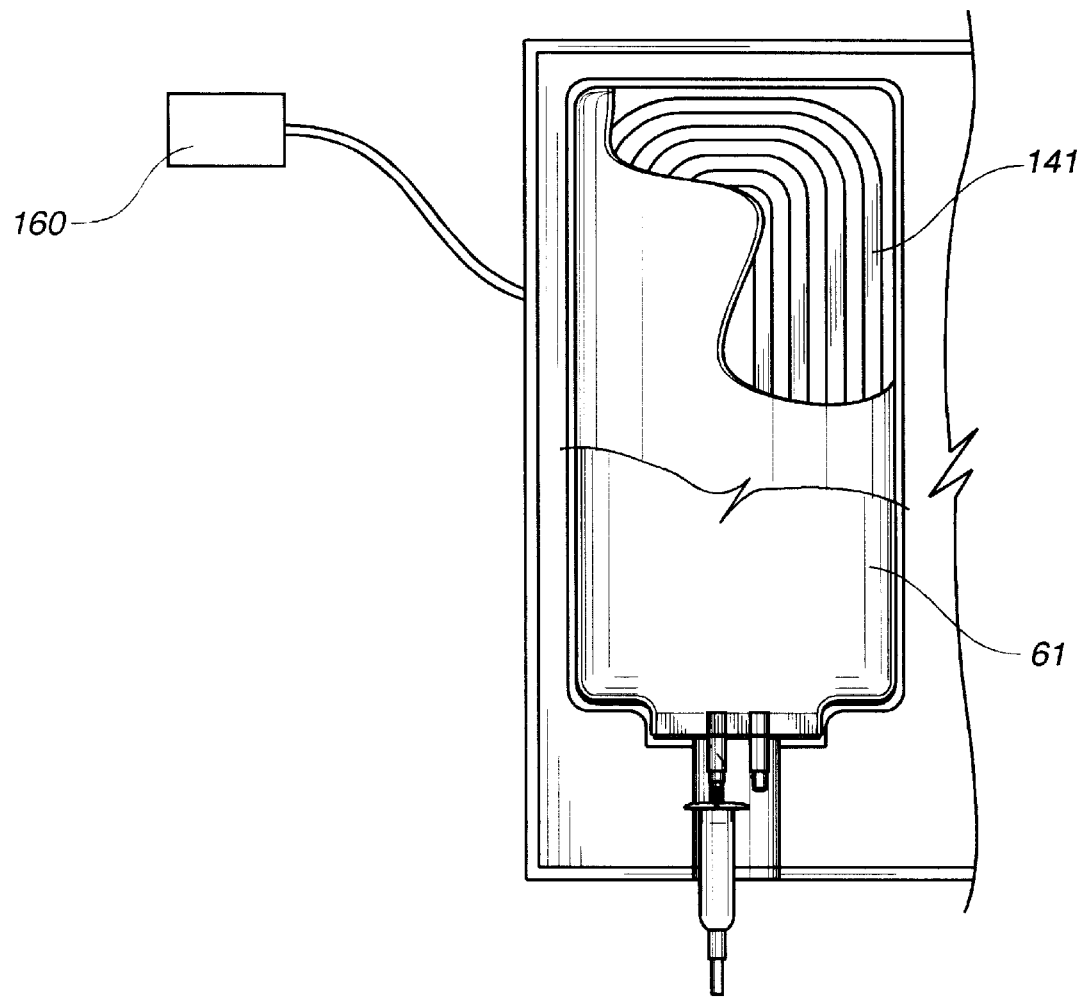
FIG. 7 depicts a plan, partial cut-away view of a portion of the embodiment of the present invention depicted in FIG. 6.
Figure 8:
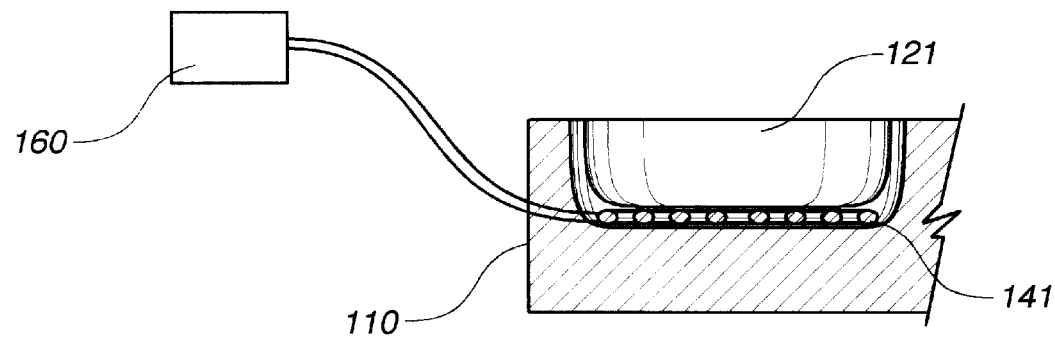
FIG. 8 depicts an end cross-sectional view of the portion of the embodiment of the present invention depicted in FIG. 7, along line 8—8.

Housing 100 may be constructed of any suitable preferably metallic material such as steel or aluminum. Plurality of plates or channels 120 should preferably be constructed of aluminum or copper or other material with sufficiently high thermal conductivity to adequately perform the important function of maintaining sequestered blood preferably at 37° C. Referring to FIGS. 1, 7 and 8, warming element 141 of a plurality of warming elements 140 is preferably contained within plate or channel 121 in housing base portion 110, with a warming affect upon blood collection bag 61 contained therein. Interconnected with power source 160, warming element 141 maintains temperature of blood sequestered in collection bag 61, and like warming elements maintain temperature of blood contained within collection bags 62, 63 and 64 seated in corresponding channels 122, 123, and 124.

Referring now to FIGS. 1 and 4, each of blood collection bags 61, 62, 63 and 64 is disposed transversely in a spaced-apart relationship in base shell portion 110. According to the present invention, each of channels 121, 122, 123, and 124 is configured to receive each of blood collection bags 61, 62, and 63 and 64 disposed transversely within base portion 110. It is also clearly shown that front wall 115 of base portion 110 is configured with plurality of slots 130 to receive plurality of tubing 45. Each of slots 131, 132, 133 and 134 is configured to receive tubing 46, 47, 48 and 49, respectively, which is then sealably attached to blood collection bag 61, 62, 63 and 64. FIG. 4 depicts tubing 47 received in slot 123 with tubing 47 attached to blood bag 63 which is seated in channel 122. Also depicted is channel 121 before blood collection bag 61 is snugly seated therein.

Referring to FIGS. 4, 7 and 8 there is seen power source 160 which provides power to a plurality of warming elements which are preferably integrated with or embedded within plurality of plate-like channels 120. Any suitable means for warming plurality of blood collection bags 60 is contemplated herein, such as heating elements disposed around the blood collection bags herein described and disposed adjacent plurality of channel plates 120. As should be evident to those skilled in the art, the heating means contemplated herein maintains the temperature of the sequestered blood within acceptable limits to optimize the performance of the various elements constituting patients' blood, preferably 37° C.

It should be understood that each warming means 141, 142, and 143, of plurality of warming means 140 performs a function similar to a warming tray which maintains the temperature of heated food. Accordingly, a simple construction such as a metallic tray or plate having a heating coil uniformly encased therein should provide sufficient warming to sustain the sequestered blood temperature within acceptable limits. For example, with an external power supply providing a conventional 120 volts, a tray-like channel contemplated by the present invention including a heating coil of at least 8 Ω should preferably be heated to about 40–41° C. to sustain the temperature of the sequestered blood at 37° C. Of course, it will be appreciated that there are many alternative ways to accomplish this purpose of maintaining sequestered blood temperature substantially at body temperature. As another example, heated water could be circulated around the plurality of blood collection bags within the housing enclosure. Thus, as will become evident to those skilled in the art, the present invention provides a sequestration-based blood transfusion procedure heretofore unknown in the art.

Prior to initiating the sequestration process as disclosed herein, the blood collection bags should preferably be primed with anticoagulant. Conventional blood collection bags hold approximately 1000 ml of blood. To prevent coagulation of blood, it is common in the art to first add citrate dextrose, a standard anticoagulant, to blood collection bags. Following the American Association of Blood Banks' requirements that at least 15 ml of citrate dextrose be added per 100 ml of blood collected in a blood bank environment, see 21 C.F.R. Part 1, § 640.4, under the procedure taught by the present invention, at least 150 ml of citrate dextrose should preferably be added to the blood collection bags; more preferably, 200 ml of citrate dextrose should be added to the blood collection bags.

Priming is accomplished by attaching a bag of anticoagulant citrate dextrose solution 70 to tubing 75 and, then, similar to the hereinbefore described retroflush procedure, retroflowing the prerequisite amount of anticoagulant into plurality of blood collection bags 60 by appropriately adjusting the position of stopcocks 36, 31, 32, 33, and 34. When this priming procedure is completed, the bag of citrate dextrose solution is superseded by a bag containing crystalloid for later application during retroflushing.

To use the closed circuit autologous sequestration reservoir system taught by the present invention an estimate is preferably made of how much blood should be sequestered. Then, flow promoting means should preferably be applied to enable the plurality of blood collection bags to receive the patient's blood. Thus, the patient should preferably be placed in a Tredelenberg position wherein the patient's blood is passively allowed to fill first blood bag 61 under the influence of gravitational forces. As will be appreciated by those skilled in the art, such gravity-driven flow promotion means may be enhanced by elevating the operating table, thereby positioning the patient's head lower than his or her legs. As will also be appreciated by those skilled in the art, if tubing 20 is interconnected with a peripheral artery, then this gravity-flow is unnecessary because the innate arterial pressure provides a sufficient flow promotion means for pumping of the blood from the patient into the blood collection bags. Of course, the Tredelenberg position is not always a benign position for a patient because it increases central venous pressure. For example, patients having decreased function of ventricular heart muscles may not tolerate a sudden increase in the central venous pressure and frequently are not placed on the operating table with elevated legs. An alternative embodiment of the present which addresses this limitation, wherein a pump provides the flow promotion means contemplated herein is introduced into the virtual venous reservoir taught by the present invention, will be described hereinafter.

Next, the blood bag is agitated frequently to assure adequate mixing of sequestered blood with anticoagulant. Once approximately 700 ml of blood has been sequestered, i.e., 700 ml of blood admixed with 200 ml of citrate dextrose, in a total volume of approximately 900–1000 ml, the retroflush procedure, as hereinbefore described in detail, is performed.

Thereafter, the patient's blood is sequestered into the remaining blood collection bags, collection bags 62, 63 and 64, respectively. During this sequestration procedure, as will be readily appreciated by those skilled in the art, of course, patients must be monitored carefully, including ECG, and arterial and central venous pressure. As should be apparent to those skilled in the art, additional monitoring is indicated in patients with severe cardiac or respiratory disorders including pulmonary artery catheters, mixed venous oximetry and transesophageal echocardiography.

It is known that during sequestration of blood, certain hemodynamic changes may occur including hypotension, tachycardia and increased cardiac output secondary to removal of blood from the circulation. For example, during blood sequestration using acute normvolemic hemodilution a patient's sequestered blood is replaced with crystalloid. In particular, for every 1 ml of blood sequestered, 3 ml of crystalloid is usually administered. A commonly used crystalloid is lactated Ringer's or Normosol manufactured by Abbott Laboratories of Chicago, Ill. Alternatively, a plasma expander such as Abbott Laboratories' Hetastarch may be administered in a ratio of 1.5/1 for every ml of sequestered blood.

As is understood by those skilled in the art, the purpose of administering such fluids concomitantly with blood sequestration is to sustain the volume of fluid in a patient's circulatory system, i.e., to achieve normovolemic conditions or normovolemia. But, it should be clear to those skilled in the art that the overall composition of a patient's blood has changed since cellular elements are being replaced with non-cellular fluids. That is, as blood is being sequestered from a circulatory system, a patient's blood supply is simultaneously being progressively hemodiluted, thereby weakening the advantages of the blood sequestration technique. Since hemodilution eventually decreases the hemoglobin content of subsequently sequestered blood, one alternative to blood sequestration using acute normvolemic hemodilution is using hypovolemic sequestration.

Hypovolemic sequestration delays administering liberal amounts of crystalloid or plasma expanders until the endpoint of sequestration has been reached. Simultaneously, pharmacologic agents are administered to sustain a patient's blood pressure. As will be understood by those skilled in the art, this technique is hypovolemic because volume status is not maintained during blood sequestration. As will be appreciated by those skilled in the art, absent pharmacologic vasoconstriction, hypotension usually accompanies hypovolemia. The pharmacologic agent, typically neosynephrine or norepinephrine, causes the venous and arterial system to vasoconstrict, thereby sustaining blood pressure. As the venous system vasoconstricts, blood is shunted from the pelvis, bowel and other large-capacity veins which normally transport a large volume of blood eventually into the arterial system. During this pharmacologic vena-arterial compartmental blood transfusion process, as it is called in the art, the various calculations that are used for acute normovolemic hemodilution are inaccurate. Accordingly, specific variables related to the extent of oxygen delivery to the patient, e.g., as arterial oxygen saturation, mixed venous saturation and cardiac output, should preferably be monitored. By assessing these variables, oxygen delivery and consumption may be closely monitored and used guides and indicia of endpoints during sequestration.

Once blood collection as described herein is complete, a blood bag should remain connected to the patient and then be placed in a receptacle that will maintain the sequestered blood at body temperature (37° C.). Under the present invention, accomplishing such a closed circuit between patient and collected blood is accomplished by using a "virtual venous reservoir." Referring specifically to FIG. 4, there is shown the preferred embodiment of virtual venous reservoir 90 comprising plurality of blood collection bags 60 disposed within corresponding plurality of transverse channels 120, contained within housing 100. Housing 100 is preferably constructed with base portion 110 and cover portion 102. Cover portion 102 is pivotally attached to base portion 110. In the preferred embodiment, cover portion 102 is attached to base 1 10 by hinges 105 A and B.

Virtual venous reservoir 90 may either be mounted on a pole to be freely mobile or be attached to the operating table. Channels 121, 122, 123 and 124 are preferably substantially rectangular in shape. In the preferred embodiment, each of these metal channels is sized to be about 12×6 inches. The bottom surface of each channel is convex and preferably about 6 inches deep. As will be appreciated by those skilled in the art, each of metal channels 121, 122, 123 and 124 serves as a blood bag compartment which abutably and snugly receives a corresponding blood collection bag 61, 62, 63 and 64, respectively, to minimize dissipation of heat from adjacent plurality of warming elements 141, 142, 143 and 144. Obviously, if too much heat is dissipated from such warming elements, then insufficient heat is transferred to the sequestered blood contained within plurality of collection bags 60 and the sequestered blood is apt to cool below the optimal 37° C. temperature.

Still referring to FIG. 4, it is seen that cover portion 102 may be pivotally closed relative to base shell portion 110 thereby enclosing housing 100 over plurality of blood bag compartments or channels 120. The closed housing creates an effective but moderate seal so that no pressure is imparted to plurality of blood collection bags 60. It is also seen that base portion 110 is connected to conventional power source 130 which heats plurality of metal channels preferably to 37° C., thereby keeping the sequestered blood sufficiently warm. It should be noted that cover portion 102 is not connected to power source 160 or an equivalent heating element because it effectively makes no continuous contact with the plurality of blood collection bags and, hence, is extraneous to the heat conduction process.

It has been found to be advantageous to rotate plurality of blood collection bags 60 in preferably 15 minute intervals to assure that citrate is adequately distributed within the sequestered blood to prevent clumping of red blood cells. In addition, it has been observed that rotation of the blood collection bags assures that heat is uniformly distributed to all elongated sides thereof, since only one such side may be placed in contact with the warming means disposed in its corresponding channel contained within housing 100.

As will be appreciated by those skilled in the art, the appropriate time to return sequestered blood to a patient is determined by several factors including amount of blood lost during surgery, hemodynamic stability, establishing of hemostasis, etc., and, of course, is decided on a patient-by-patient basis. Generally, sequestered blood is returned to the patient when most of the surgical procedure that implicates hemorrhage has been completed.

To initiate return of the sequestered blood, a blood collection bag of plurality of collection bags 60 is lifted from the virtual venous reservoir taught by the present invention, the appropriate valve contained in valve assembly 30 is rotated into the open position, and then the sequestered blood is returned to patient 10 through tubing 20. Power source 160 to virtual venous reservoir 90 is disconnected when the last blood collection bag is removed from its corresponding channel or compartment.

More particularly, referring to FIGS. 1–4, blood collection bag 61 is lifted from its compartment 121 in reservoir 90 and preferably attached to a pole (not shown) proximal to patient 10. As will be appreciated by those skilled in the art, blood collection bag 61 is preferably positioned upon this pole at approximately 5–7 feet above the floor. Valve 31 is then opened to enable blood flow through flexible tubing 46 through coupling 51 and then through tubing segment 26 into valve assembly 30 then through flexible tubing 20 and into the patient's circulatory system via catheter 15. The rate of flow of blood through this tubing may, of course, be varied by adjusting clamp 66 attached to tubing 46. It should be clear that blood is inherently prevented from flowing back through valve 31 and clamp 66 because they are essentially closed to flow in that direction. After sequestered blood contained in blood collection bag 61 has been completely returned to the patient, valve 31 is closed and then valve 32 is opened and sequestered blood is similarly allowed to flow through flexible tubing 47 and tubing segment 27 through valve assembly 30 then through flexible tubing 20 and into the patient via catheter 15 as herebefore described. Similarly, sequestered blood is permitted to flow through the remaining portions of tubing assembly 24, in turn, back to the patient.

Figure 5:
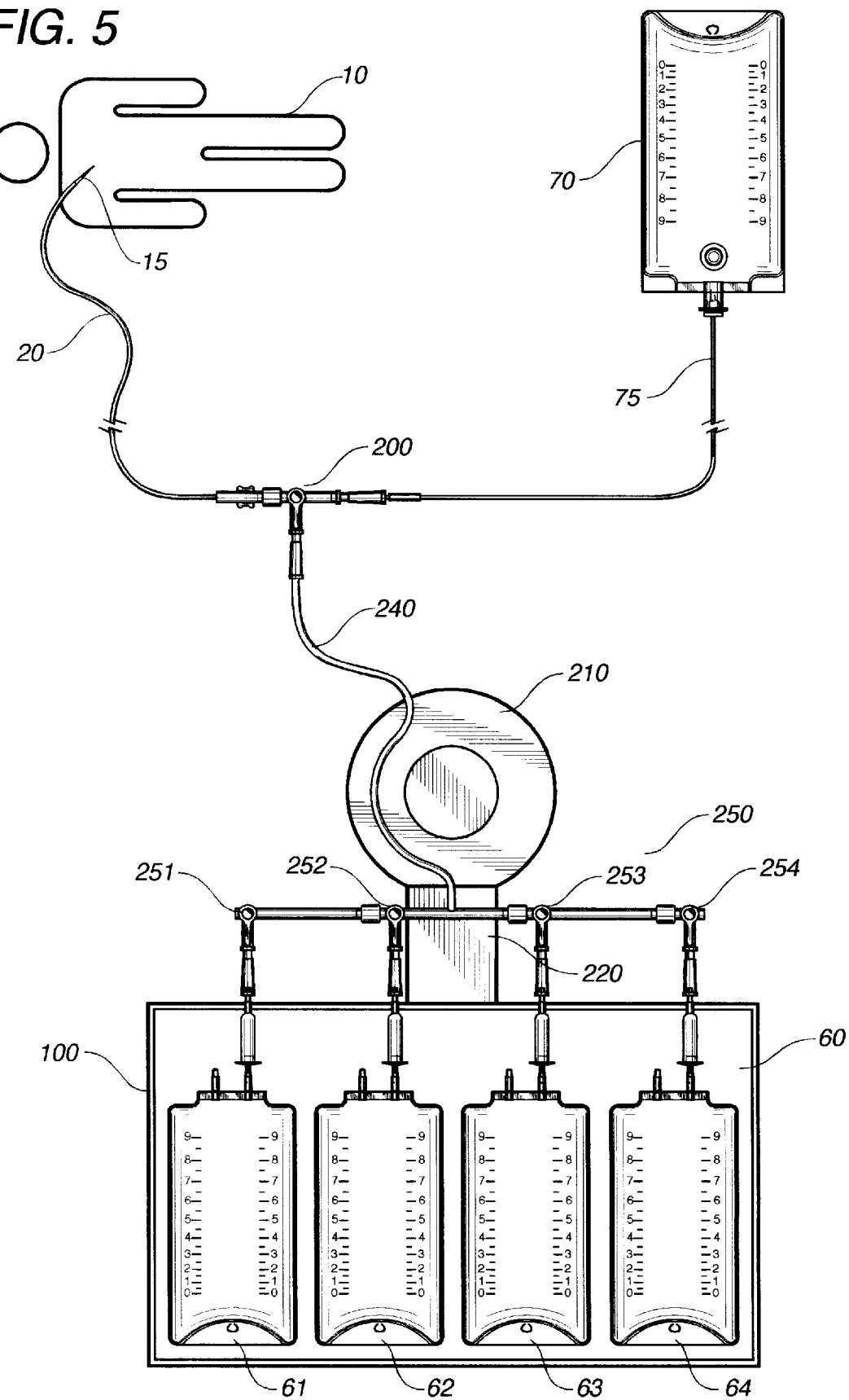
FIG. 5 depicts a simplified front view showing an alternative embodiment of the present invention interconnected with a patient.
Figure 6:
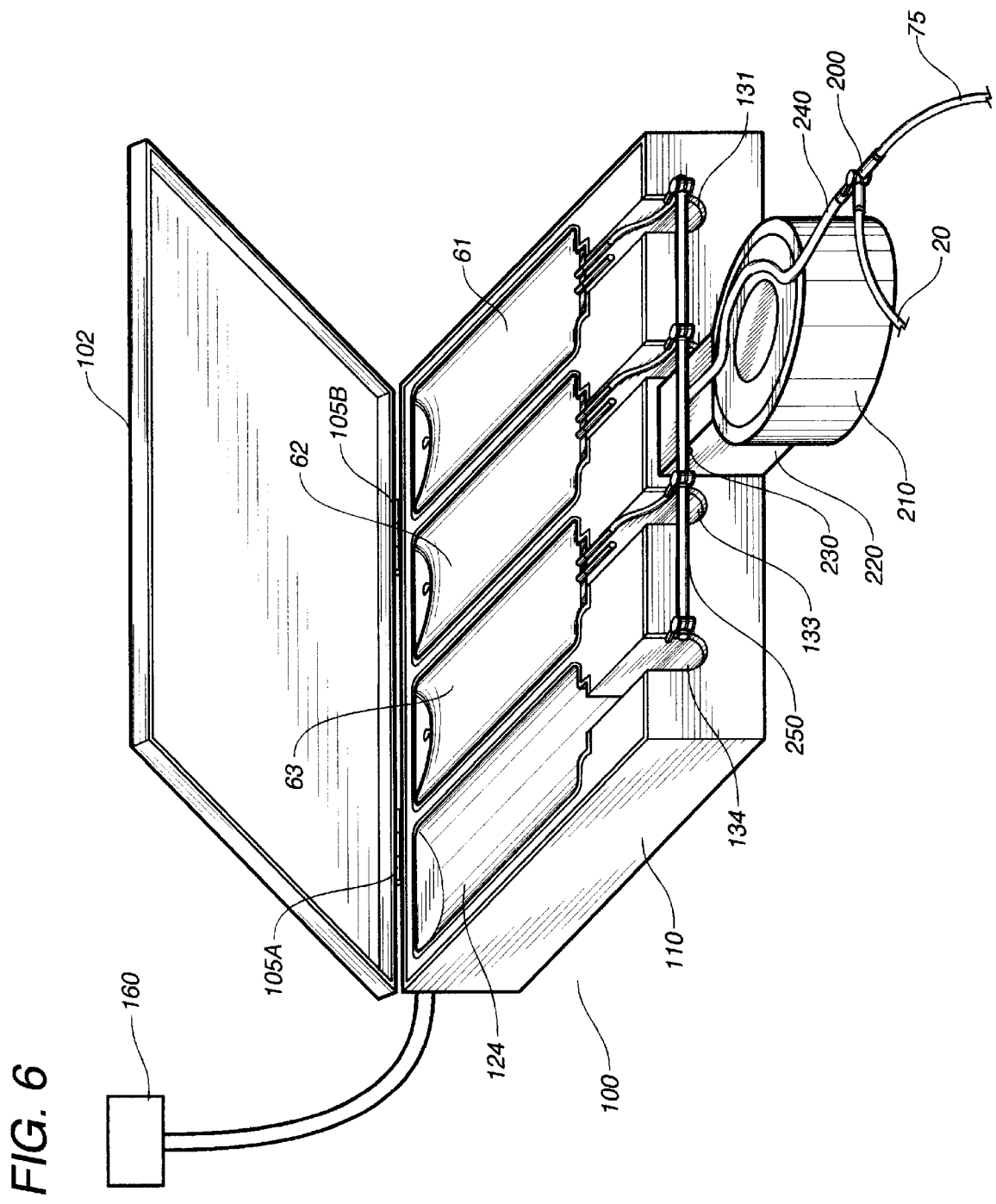
FIG. 6 depicts a simplified frontal perspective view of a portion of the alternative embodiment of the present invention depicted in FIG. 5.

Now referring to FIGS. 5 and 6, there is depicted an alternative embodiment of the present invention which includes pumping means to provide the prerequisite forces to overcome inertial effects so that blood sequestration and reinfusion may be performed as described herein. That is, instead of urging sequestration and reinfusion via the influence of gravity and venous pressure, external pressure may be supplied. It will be appreciated by those skilled in the art that such external pressure is advantageous under circumstances in which a patient has low venous pressure or in which gravity-driven venous collection is not practicable. Furthermore, while blood sequestration should preferably be completed prior to commencing surgery, this is not always the case. Occasionally, sequestration continues during the early phases of surgery such as when a surgeon makes the initial incision and surgical approaches; it may accordingly not be practicable to sustain a patient in a steep Tredelenberg position because the surgeon must perform the indicated procedures.

While cycling of sequestered blood back to a patient is typically passively performed, the cycling procedure may be improved using standard pressure bags which encase the blood collection bags. Pressure in these bags ranging from 150–300 mm Hg may be used to provide flow promoting means by causing acceleration of blood flow in the network of interconnected flexible tubing. It will be appreciated, however, that a significant disadvantage of this approach can be that pressure per se may damage certain cellular components of blood, most notably platelets.

Incorporating a pump into the closed system taught by the present invention affords advantages over techniques known in the art. During blood sequestration, a pump means would provide more flow control and predictability to the blood collection procedure. Furthermore, under suitable operating circumstances, this alternative embodiment of a sequestration reservoir system could improve the versatility of the present invention: blood could be sequestered during the preoperative phase, during post-anesthesia induction presurgical phase, and even during the early surgical phase prior to any significant surgical blood loss. Based upon a patient's hemodynamic response, sequestration could be intermittently accelerated by varying pump speeds. Upon completion of surgery, blood could be cycled back to the patient at a controlled rate using a pump as will be hereinafter described. As will be understood by those skilled in the art, the pump could also be used during anticoagulant priming and retroflush techniques hereinbefore described.

Now referring specifically to FIGS. 5 and 6, there is depicted an embodiment of the present invention which uses a suitable pump to provide sufficient blood flow promotion to enable autologous blood sequestration as taught herein. In particular, FIG. 5 is a simplified view of the preferred embodiment depicted in FIG. 1, but including pump 210. As will become apparent to those skilled in the art, pump 210 establishes fluid communication with blood collection bags 60 and is attached to manifold 220 which is, in turn, attached to front 115 of base portion 110 of housing 100. Valve assembly 300 is received in gutter 230 which is disposed upon manifold 220.

In one embodiment of the present invention, manifold 220 comprises a metal bar approximately two square inches with gutter 230 approximately 0.5 inches deep and 0.25 inches wide. As contemplated by the present invention, gutter 230 is configured so that once seated therein, valve assembly 300 is both secure and immobile. It has been found that to avoid damage to cellular elements of blood, pump 210 should preferably be a low-flow, bi-directional device, functioning as an actuator because it promotes the actual sequestration of patients' blood.

Examples are roller or peristaltic pumps which force blood through tubing by rolling a compression system along the tubing in a circular motion. Typically, in operation, sequestered blood contacts the tubing compression region for about 30 minutes. Representative pumps are 3M Sarns 9000 Universal Roller Pump or 3M Sarns Modular Perfusion System Roller Pump manufactured by 3M Sarns Healthcare of Ann Arbor, Mich.; Model 043600000 Precision Blood Pump manufactured by Cobe Laboratories. An another pump which has been found to be applicable under the present invention is a centrifugal pump which invokes centrifugal force to urge blood flow within the network of flexible tubing described herein. Such centrifugal pumps use vaned impellar of a nest of plastic cones contained within a plastic housing. Theoretically, a centrifugal pump is preferable to a roller pump because there is less likelihood of trauma to blood elements, since there is no compression of a tube, i.e., centrifugal pumps are non-occlusive. Either vortex-based centrifugal pumps may be used, e.g., Biomedicus Model BP 80 or Model BP 50 manufactured by Medtronic, Inc. of Minneapolis, Minn. or non-vortex-based pumps may be used, e.g., Sarns Delphin manufactured by 3M Sarns Healthcare.

Still referring to FIGS. 5 and 6, it is seen that the flexible tubing assembly and the valve assembly taught by the present invention (depicted in FIGS. 1–4) have been modified to accommodate and integrate manifold 220 and actuator pump 210 into another embodiment of a closed circuit autologous sequestration reservoir system. Flexible tubing 20 is interconnected with valve 200 which controls the flow of blood, saline solution or anticoagulant into flexible tubing 240. Tubing 240 is then interconnected with actuator pump 210. The pumped fluid is then received into valve assembly 250 which distributes blood, saline solution or anticoagulant into blood collection bag 61, 62, 63 or 64 preferably through stopcock 251, 252, 253 or 254, respectively. Thus, under the teachings of the present invention, tubing 75 which transports either anticoagulant or saline solution, during priming or retroflushing steps, respectively, is now connected directly to stopcock 200. Thus, this stopcock is now preferably removed from the valve assembly which feeds blood into plurality of blood collection bags 60 contained within housing 100.

Thus, to prime this embodiment of the sequestration system contemplated by the present invention, citrate anticoagulant bag 70 is interconnected with tubing 75 and stopcock 200 is opened so that citrate flows through tubing 240 into actuator pump 210. Next, as hereinbefore described in detail, sufficient anticoagulant is sequentially pumped into blood collection bags 61, 62, 63 and 64, in turn, and then tubing 75 is closed off at stopcock 200. As should be evident to those skilled in the art, to sequester blood into blood collection bags 60, pump 210 is activated to promote blood flow from patient 10 through catheter 15 into tubing 20 and then into tubing 240 and through valve assembly 250. As hereinbefore described, as each blood collection bag is filled, retroflushing is performed to clear residual blood from tubing depending from a stopcock of valve assembly 250. Thus, once blood collection bag 61 is filled, retroflushing is performed from bag 70 containing saline solution through tubing 75 and open stopcock 200 into tubing portions associated with stopcock 251.

Similar retroflushing is performed as blood collection bags 62, 63 and 64 are filled through stopcocks 252, 253 and 254, respectively. Similarly, once it is established that sequestered blood may be returned to the patient, the flow direction of the actuator pump is changed, appropriate stopcocks of valve assembly 250 are sequentially opened, and sequestered blood is pumped back to the patient. As will be appreciated by those skilled in the art, during surgery, actuator 210 may be opened and sequestered blood be allowed to slowly trickle back to the patient, thereby mimicking venous circulation.

According to the present invention, preferably at least three flow settings should be available via the actuator pump: 50 ml/min, 100 ml/min and 150 ml/min. Such flows enable the prerequisite priming, sequestration and retroflushing maneuvers hereinbefore described in detail. It will be appreciated by those skilled in the art that these flow rates are selected to promote adequate fluid flow but to simultaneously be sufficiently low not to tend to damage blood elements or to emulate the behavior of a rapid infuser. Hence, a flow rate of 150 ml/min could be used priming and retroflusing. A flow rate of 100 ml/min is advantageous during sequestration wherein each blood collection would become full after about 10 minutes of sequestration. It has been found that a flow rate of 50 ml/min is advantageous for cycling sequestered blood back to a patient.

According to the present invention, the blood sequestration system must be completely recycled upon return of the sequestered blood. Therefore, as will be understood by those skilled in the art, all sequestered blood must be returned to the patient. It is a distinct feature and advantage of the present invention that there is no storage of blood beyond the immediate operating room environment. Similarly, the present invention teaches that there should be no disconnection of any blood collection bag from the blood sequestration system. Otherwise, the benefits of the present invention will not be fully realized because its performance will be reduced to emulate that typical blood bank. Such deviation from the teachings of the present invention will render the blood delivery system objectionable and unacceptable to adherents of strict religious convictions regarding blood banking practices hereinbefore described.

It should be clearly understood that another embodiment of the present invention may be constructed with only two blood compartments instead of four compartments as described in the preferred embodiment. As will, of course, be appreciated by those skilled in the art, under circumstances in which less aggressive blood sequestered is anticipated or, indeed, feasible, then only a two-blood collection bag apparatus would be needed.

It is also within the contemplation of the present invention to provide an embodiment which is suitable for pediatric patients, wherein the scale of the components of the autologous sequestration reservoir taught herein is reduced to be commensurate with the blood flow of children. For example, the compartments of the present invention might be reduced 50% to accommodate smaller blood collection bags which are appropriate for collecting smaller volumes of sequestered blood. It has been ascertained that a two-compartment apparatus is typically suitable for sequestering blood from pediatric patients. According to the teachings of the present invention, an improved apparatus is provided which sustains a closed circuit relationship between a patient and the patient's blood during a blood sequestration procedure.

It is an important feature and advantage of the present invention that an apparatus and method are provided for controlling a patient's blood supply immediately before, during and immediately after surgery, wherein the patient's blood maintains continuous contact with the patient. Unlike prior art devices, the present invention teaches a simple apparatus comprising a novel blood bag assembly which forms a closed circuit autologous sequestration reservoir system with a patient. In addition, as will be appreciated by those skilled in the art, the prior art has been significantly improved because the present invention avoids unsettled issues associated with allogeneic blood products while simultaneously providing a system for sequestering blood while avoiding all allogeneic blood products, thereby being acceptable to patients who have religious or health based objections to use of allogeneic blood. Thus, the present invention provides a system for performing normovolemic hemodilution, pharmacologic vena-arterial compartmental translocation, hypovolemic hemodilution and modifications thereof, which is acceptable to patients who have religious or health-based objections to use of allogeneic blood products and is even compatible with the religious beliefs of the Jehovah's Witnesses.

Accordingly, the present invention produces unexpectedly advantageous results over the prior art which overcome disadvantages inherent in conventional intraoperative blood salvage procedures and concomitant autotransfusion, and also inherent in predonation procedures. Furthermore, it should be evident that the present invention provides an apparatus and method which economically and simply affords a warming environment for sequestered blood, thereby sustaining integrity and sterility of the sequestered blood. Furthermore, the system taught by the present invention sustains the collected blood temperature at normal body temperature.

Another aspect of the present invention is to promote optimal platelet functionality and longevity by providing suitable agitation means to the plurality of blood collection bags described herein. Sufficiently gentle agitation means that have been considered by those skilled in the art as being applicable to blood collection and storage include rotators, flatbed or platform agitators, tumblers, and ferris wheel configured agitators. For example, rotators are generally available in configurations of 1, 2, and 6 RPM in either circular (face-over-face) or elliptical (side-over-side) angle of rotation. As another example, flatbed agitators typically have 1 to 1½ inch lateral excursion at 70 RPM. It will be understood that not all agitators are compatible with all types of blood collection bags. Researchers in the art have discovered that flatbed agitation means tends to preserve platelet functionality superior to rotating agitation means theoretically due to platelet-plastic bag interactions generated at various shear stresses and the like. As an illustration, applying 6 RPM elliptical rotators to blood stored in PL-732 blow-molded polyolefin bags was found to engender unacceptable post-transfusion platelet recovery and survival. See, S. Murphy, R. A. Kahn, S. Holme, and G. L. Phillips, "Improved Storage of Platelets for Transfusion in a New Container" published in Blood, 60:194:200 (1992). Acceptable platelet longevity results have been achieved agitating these bags on a flatbed agitator at 70 RPM.

Referring now to FIGS. 10A, B and C, there is depicted an embodiment of the present invention having slot assembly 300 comprising plurality of pivotable channel means 330. Unlike the embodiment of the present invention depicted in FIG. 4 with plurality of fixed channel means 130, the embodiment depicted in FIGS. 10A and B is configured with each channel 321, 322, 323, and 324 of plurality of channel means 330 to rotate side-to-side about a vertical axis disposed perpendicularly of the bottom of collection bag housing 390 (not shown) which is, of course, configured similar to housing 100 depicted in FIG. 4. As specifically shown schematically by the side view of channel means 324, representative of each channel means of plurality of channel means 330 in FIG. 10C, each channel or tray means 321, 322, 323, or 324, is caused to rock from side-to-side about its vertical axis (depicted by numeral v) by motor-driven gear assembly 360. Thus, channel means 324 is shown rocking from vertical position v along its vertical, pivoting axis to right position $v_R$ then back through vertical position v to left position $v_L$. Accordingly, in a conventional manner well known in the art, motor 360 drives primary gear 365 which, in turn, causes each of secondary gears 371, 372, 373, and 374 of plurality of secondary gears 370 to rock or rotate proportionally, alternately in both directions relative to the vertical axis. As will be appreciated by those skilled in the art, the movement of plurality of secondary gears 370 thereby causes side-to-side rotation of plurality of channel means 321, 322, 323, and 324. The preferable rotational speed of each of the channel means should be about one rock per every 3–4 seconds or 40 RPM.

It will be understood that, instead of rocking plurality of channel means 330 from side-to-side about a vertical axis, the objects of the present invention may also be achieved by incorporating a suitable gear mechanism to move each channel of plurality of channel means 330 horizontally from side-to-side, thereby emulating a flat-bed agitator. Thus, referring specifically to FIGS. 11A, B and C, one of plurality of hinge means 340 is disposed beneath each channel means of plurality of channel means 330. Movements of primary gear 365 powered by motor 360 cause each of preferably ball bearing hinge means 341, 342, 343, 344 of plurality of hinge means 340 to, in turn, cause linear movement of each channel 321, 322, 323, 324 in a horizontal plane parallel to the base of a collection bag housing described herein (movement shown in FIG. 11C, similar to movement shown in FIG. 10C). According to the present invention, it is contemplated that this horizontal, flat-bed like movement would be about 60 RPM.

It will be understood by those skilled in the art that in order to accommodate the movement mechanisms for either vertical rotation or for horizontal linear movement, the configuration depicted in FIG. 4 must be modified accordingly. That is, more space must be available between each of plurality of channels 330 (shown in both FIGS. 10A and B and in FIGS. 11A and B) than between each of plurality of channels 130 (shown in FIG. 4).

Another feature and aspect of the present invention is to provide an external source of oxygen into each collection bag as hereinbefore described in detail. Referring to FIGS. 12, 13, and 14 there is depicted embodiments of the present invention which infuse oxygen into a patient's sequestered blood. More particularly, referring specifically to FIGS. 12 and 13, there is shown for blood collection bag 400 containing tube assembly 410 which is in fluid communication with oxygen source S through connector tube 440. As clearly shown, tube inlay assembly 410 is preferably constructed with a plurality of spaced-apart orifices 450 to transport oxygen from source S into sequestered blood B. In a manner well known in the art, tube assembly 410 should be configured to uniformly disperse or "bubble" oxygen throughout the sequestered blood. It has been found that having a triplicate row comprising central portion 412 and lateral portions 414 and 416 provide an adequate delivery of oxygen as contemplated under then present invention. As will be understood by those skilled in the art, an oxygen flow of approximately 25–50 ml/min should be sufficient. Oxygen supply S may be either a piped-in supply of oxygen or a conventional oxygen tank having a flow meter attached thereto.

Similar to any closed system into which there is a flow of pressurized fluid, provision must be made for pressure-relief, for safety purposes. Since under this embodiment of the present invention, oxygen is flowing into a plurality of blood collection bags, oxygen pressure could reach a threshold wherein one or more collection bags might burst. Accordingly, as depicted in FIG. 14, showing plurality of oxygen bubbles OB dispersed throughout sequestered blood B contained within blood collection bag 400. As previously described, oxygen is delivered into bag 400 from source S through conduit means 440. Also shown is blood collection conduit means 405. As will be appreciated by those skilled in the art, blood collection bag 400 is preferably constructed with suitable exhaust or "pressure venting" means 451. Such pressure relief could be achieved by attaching small plastic housing 452 in an end of collection bag 400; in a manner well known in the art, housing 452 would be opened automatically when, and if, oxygen flow into bag 400 through entry means 440 causes internal bag pressure to reach about 5–10 mm Hg. Alternatively, the pressure relief means contemplated by the present invention could be a one-way pressure-relief valve. Thus, such a pressure-relief valve 451 would automatically open when oxygen pressure in collection bag exceeds a predetermined threshold value. As seen in FIG. 14, preferably plastic housing 452 protrudes beyond the outer surface of blood collection bag 400 to assure that if blood sequestered in bag 400 also enters housing 452, then this blood is prevented from exiting the blood collection bag. Semipermeable membrane means 455 has been found to provide a suitable exit for excess oxygen while providing a barrier to the passage of blood. Such a barrier would also prevent blood from being inadvertently discharged from a collection bag when such bag is being moved or perhaps lifted from its channel.

For example, a polycarbonate-track-etch membrane marketed under the trade name PORETICS by Osmonics of Minnetonka, Minn. provides the prerequisite barrier to blood passage and is both neutral biologically and non-cytotoxic. In particular, to prevent passage of cellular elements of blood through such a membrane, since the smallest of such elements, namely, platelets, have a diameter in the range of 2–4 $\mu$m, a pore size of 1 $\mu$m is preferable. Those skilled in the art will appreciate that use of a membrane with such a pore size will prevent a solution having a mean molecular weight greater than 100,000 Daltons from passing through. Since the mean molecular weight of the components of blood plasma, including proteins and various electrolytes such as albumen, globulin, sodium, magnesium, etc., are much greater than 100,000 Daltons, it is clear that blood flow will be effectively stopped at this membrane 455 (FIG. 14).

Now referring collectively to FIGS. 10A–C, 11A–C, and 12–14, to urge migration of oxygen throughout the sequestered blood and to the top portion of each bag of the plurality of blood collection bags taught by the present invention, it has been found to be advantageous to angulate channel/gear assembly 350 as shown in FIG. 14. That is, by biasing the exhausting of bubbled oxygen to the exterior portion of collection bag 400, maximal dispersion of the oxygen is accomplished.

As will be appreciated by those skilled in the art, sufficient accommodation should be made for the prerequisite movement of the channel/gear assembly to agitate the plurality of bags as hereinbefore described and, of course, to facilitate the travel of the plethora of oxygen bubbles throughout the plurality of blood collection bags. The configuration of the cover of the virtual venous reservoir taught by the present invention should preferably be modified from the configuration depicted in FIG. 4 in order to accommodate the plurality of vent means and angled disposition of the plurality of channels depicted in FIG. 14, and the agitation means depicted in FIGS. 10A, B and 11A, B. It will be understood that essentially all other aspects of the virtual venous reservoir would remain the same.

FIG. 15 is a simplified top plan view showing an embodiment of the present invention in which an actuator or auxiliary pump means 610 is provided for quantitative fluid replacement of a patient's blood. For example, assuming volume for volume replacement, if a patient's blood is being sequestered at the rate of 200 ml/min, the fluid return would be actuated at the same rate of 200 ml/min; this fluid replacement would be accomplished by an appropriately set auxiliary pump as herein described. If, on the other hand, only 2:1 replacement is advantageous, then the pumping provided by actuator pump means 610 would be 100 ml/min so that for every 200 ml of blood sequestered from a patient, only 100 ml of replacement fluid would be administered.

Accordingly, as a modification of normovolemic hemodilution as hereinbefore described and depicted in FIGS. 5–6 for the administration of fluid to replace withdrawn blood and to thereby maintain circulatory stability using pump means 210, a supplementary pumping mechanism is provided which returns fluid to a patient in a controlled manner as blood is being sequestered from the patient's circulatory system. There is seen in FIG. 15 an embodiment of the virtual venous reservoir 590 taught by the present invention including housing 600 containing plurality of blood collection bags 560, in fluid communication with actuator pump means 510 and auxiliary pump means 610. Auxiliary pump means 610 is in fluid communication with crystalloid or colloid 570. It will become evident to those skilled in the art that the instantly described procedure is effectively a "hypovolemic hemodilution" because it attempts to enhance the Hb content of sequestered blood.

It will be understood by those skilled in the art that, as hereinbefore described in detail, when blood is sequestered and replaced with crystalloid as contemplated under the present invention, a patient progressively becomes hemodiluted. That is, for every succeeding unit of blood sequestered, the Hb or Hematocrit progressively becomes less and less. Accordingly, if this progressive reduction of the Hb or Hematocrit is slowed, i.e., if returning fluid to the patient is delayed wherein more volume is being sequestered from the patient than is being returned, then a mild state of hypovolemia occurs. As hereinbefore described, to support a patient's circulation under these conditions, pharmacologic vasoconstriction might be necessary to avoid the onset of hypotension. Embodiments of the present invention having the benefit of two pump means as taught herein enable a controlled method for accomplishing hypovolemic hemodilution in patients. For example, in a young patient, 1,000 ml of blood could be sequestered while only 500 ml of Hespan (hetastarch) is returned to this patient. As another example, in an elderly patient, on the other hand, a more conservative approach might be taken wherein perhaps 800 ml of Hespan would be returned, thereby creating a reduced volume deficit of only 200 ml. As another illustration of the advantages of the two-pump methodology taught by the present invention, is when colloid solutions and the like are being used in conjunction with hetastarch causing increase of patients' intravascular compartments. The instant methodology provides a convenient means for compensating for this volume expansion by enabling the sequestration of a calculated volume of blood prior to the infusion of hetastarch.

Therefore, incorporation of auxiliary pump means 610, i.e., preferably either a roller of centrifugal pump, disposed laterally of actuator pump means 510 and on the side 605 of housing 600 proximal to crystalloid 570. As contemplated by the present invention, pump means 610 functions as an auxiliary actuator wherein fluid replacement in the form of crystalloid or colloid is achieved simultaneously with blood sequestration as taught herein. It should be clear to those skilled in the art that the present invention provides a safe and reliable system for administering collected blood to a patient, after surgery, at varying rates of delivery. The closed and uninterrupted system disclosed herein for sequestering blood into collection bags from a patient and then for transfusing the sequestered blood to the patient, inherently foregoes the normally recommended 6-hours' refrigeration requirements after blood sequestration. Accordingly, more effective, safe and reliable transfusion may be performed using the present invention than have been otherwise attainable heretofore.

Other variations and modifications will, of course, become apparent from a consideration of the structures and techniques hereinbefore described and depicted. Accordingly, it should be clearly understood that the present invention is not intended to be limited by the particular features and structures hereinbefore described and depicted in the accompanying drawings, but that the present invention is to be measured by the scope of the appended claims herein.

What is claimed is:

1. A closed circuit autologous blood sequestration reservoir system for sequestering blood from and cycling said sequestered blood to a patient disposed upon a table, prior to, during and after surgery, said system comprising:

a plurality of oxygenated blood collection bags, each containing a tube inlay assembly in fluid communication with an oxygen source, for sequestering blood from said patient;

a valve assembly having a plurality of valves disposed medially between said plurality of oxygenated blood collection bags and said patient, for controlling cycling of said sequestered blood from and to said patient through a plurality of flexible tubing;

each of said plurality of oxygenated blood collection bags configured with a plurality of receptacles disposed at one end thereof for sealably attaching to a tube of said plurality of flexible tubing;

anticoagulant means stored within an anticoagulant container disposed proximal of said plurality of flexible tubing for preventing coagulation of said sequestered blood in said plurality of flexible tubing and in said plurality of oxygenated blood collection bags;

each flexible tube of said plurality of flexible tubing interconnected with a corresponding valve of said plurality of valves of said valve assembly;

flexible anticoagulant tubing interconnected with said anticoagulant container and a valve of said plurality of valves of said valve assembly for delivering said anticoagulant means into said plurality of oxygenated blood collection blood bags and said plurality of flexible tubing interconnected therewith;

a flexible catheter tubing for interconnecting said valve assemble with said patient;

a portable housing including a base portion having a longitudinal axis for receiving said plurality of oxygenated blood collection bags in said base portion and a shell portion pivotally attached to said base portion for covering said plurality of oxygenated blood collection bags in said base portion;

said base portion further having a first longitudinal wall disposed at an end of said base portion where said shell portion is pivotally attached thereto, and further having a second longitudinal wall disposed at an end of said base portion opposite of said first longitudinal wall;

said base portion further having warming means configured to abutably receive said plurality of oxygenated blood collection bags for maintaining said sequestered blood at a temperature of 37° C.;

flow promoting means applied to said flexible catheter tubing for urging flow of said patient's blood from said flexible catheter tubing to said plurality of oxygenated blood collection bags.

2. The closed circuit autologous blood sequestration reservoir system recited in claim 1, wherein said base portion of said housing comprises a plurality of parallel channels disposed along said longitudinal axis of said base portion and configured for each channel of said plurality of channels abutably receiving one of said plurality of oxygenated blood collection bags.

3. The closed circuit autologous blood sequestration reservoir system recited in claim 2, wherein said housing further comprises a plurality of slot means disposed in said second longitudinal wall of said base portion and also disposed contiguously of said plurality of channels, with each slot of said plurality of slots configured to receive a portion of a flexible tubing of said plurality of flexible tubing, with each of said portions of flexible tubing of said plurality of flexible tubing emanating from said plurality of oxygenated blood collection bags disposed in said plurality of channels, for promoting an adiabatic environment of said plurality of blood collection bags abutably received within said plurality of channels enclosed within said housing.

4. The closed circuit autologous blood sequestration reservoir system recited in claim 3, wherein said warming means comprises heating coil means contained within said plurality of channels and interconnected with an external power source.

5. The closed circuit autologous blood sequestration reservoir system recited in claim 3, wherein said portable housing means comprises agitation means rotatably attached to said housing means for rotating each of said plurality of oxygenated blood collection bags within each of said corresponding plurality of slot means.

6. The closed circuit autologous blood sequestration reservoir system recited in claim 1, wherein said flow promoting means comprises placing said patient in a position in which an end of said table is raised to lower said patient's legs relative to said patient's head so that said patient's blood is gravity-driven from said flexible catheter tubing to said plurality of oxygenated blood collection bags.

7. The closed circuit autologous blood sequestration reservoir system recited in claim 1, wherein said flow promoting means comprises pump means disposed adjacent said housing and in fluid communication with said valve assembly.

8. The closed circuit autologous blood sequestration reservoir system recited in claim 1, wherein said valve assembly comprises a plurality of stopcocks configured so that each of said plurality of stopcocks receives one tube of said plurality of flexible tubing.

9. The closed circuit autologous blood sequestration reservoir system recited in claim 1, wherein said tube assembly includes a plurality of spaced-apart orifices configured to transport oxygen from said oxygen source to said sequestered blood.

10. The closed circuit autologous blood sequestration reservoir system recited in claim 1, wherein each of said plurality of oxygenated blood collection bags comprises a pressure-relief means for discharging excess oxygen without discharging said oxygen from said oxygenated sequestered blood.

11. The closed circuit autologous blood sequestration reservoir system recited in claim 1, wherein each of said plurality of oxygenated blood collection bags comprises auxiliary pump means in fluid communication with said anticoagulant means for controlling dilution of said oxygenated sequestered blood.

12. A method for sequestering a patient's blood into a closed circuit autologous blood sequestration reservoir and for cycling said sequestered blood to said patient, prior to, during and after surgery, said method comprising the steps of:

estimating a quantity of said patient's blood to be sequestered;

attaching a flexible catheter tubing to said patient;

priming with a first anticoagulant a plurality of flexible tubing interconnected with said flexible catheter tubing;

further priming with said first anticoagulant a plurality of blood collection bags corresponding to and interconnected with said plurality of flexible tubing;

force-feeding said patient's estimated blood into said flexible catheter tubing and then through said plurality of flexible tubing and then into said plurality of blood collection bags;

controlling said flow of said sequestered blood through said plurality of flexible tubing into and from said plurality of blood collection bags;

oxygenating said sequestered blood;

agitating said sequestered blood contained in said plurality of blood collection bags;

warming said sequestered blood to maintain a temperature of 37° C.;

recycling said sequestered blood from said plurality of blood collection bags through said plurality of flexible tubing through said flexible catheter tubing into said patient; and retroflushing with a second anticoagulant said plurality of flexible tubing and said plurality of blood collection bags, for purging said sequestered blood from said plurality of flexible tubing and from said plurality of blood collection bags.

13. The method for sequestering a patient's blood into a closed circuit autologous blood sequestration reservoir recited in claim 12, wherein said retroflushing step comprises sequentially flushing each tube of said plurality of flexible tubing.

14. The method for sequestering a patient's blood into a closed circuit autologous blood sequestration reservoir recited in claim 13, wherein said retroflushing step further comprises sequentially flushing each blood collection bag of said plurality of blood collection bags.

15. The method for sequestering a patient's blood into a closed circuit autologous blood sequestration reservoir recited in claim 12, wherein said priming step comprises sequentially priming each tube of said plurality of flexible tubing.

16. The method for sequestering a patient's blood into a closed circuit autologous blood sequestration reservoir recited in claim 12, wherein said further priming step comprises sequentially priming each blood collection bag of said plurality of blood collection bags.

17. The method for sequestering a patient's blood into a closed circuit autologous blood sequestration reservoir recited in claim 12, wherein said first anticoagulant comprises citrate dextrose.

18. The method for sequestering a patient's blood into a closed circuit autologous blood sequestration reservoir recited in claim 12, wherein said warming step comprises confining said plurality of blood collection bags within an adiabatic enclosure.

19. The method for sequestering a patient's blood into a closed circuit autologous blood sequestration reservoir recited in claim 12, wherein said warming step comprises contacting said plurality of blood collection bags with heating coils interconnected with an external power source.

20. The method for sequestering a patient's blood into a closed circuit autologous blood sequestration reservoir recited in claim 12, wherein said second anticoagulant comprises a saline solution.

21. A closed circuit autologous blood sequestration reservoir system for sequestering blood from and cycling said sequestered blood to a patient disposed upon a table, prior to, during and after surgery, said system comprising:

a plurality of oxygenated blood collection bags, each containing a tube inlay assembly in fluid communication with an oxygen source, for sequestering blood from said patient;

a valve assembly having a plurality of valves disposed medially between said plurality of oxygenated blood collection bags and said patient, for controlling cycling of said sequestered blood from and to said patient through a plurality of flexible tubing;

each of said plurality of oxygenated blood collection bags configured with a plurality of receptacles disposed at one end thereof for sealably attaching to a tube of said plurality of flexible tubing;

anticoagulant means stored within an anticoagulant container disposed proximal of said plurality of flexible tubing for preventing coagulation of said sequestered blood in said plurality of flexible tubing and in said plurality of oxygenated blood collection bags;

each flexible tube of said plurality of flexible tubing interconnected with a corresponding valve of said plurality of valves of said valve assembly;

flexible anticoagulant tubing interconnected with said anticoagulant container and a valve of said plurality of valves of said valve assembly for delivering said anticoagulant means into said plurality of oxygenated blood collection bags and said plurality of flexible tubing interconnected therewith;

a flexible catheter tubing for interconnecting said valve assembly with said patient;

a portable housing including a base portion having a longitudinal axis for receiving said plurality of blood collection bags in said base portion and including a shell portion pivotally attached to said base portion for covering said plurality of oxygenated blood collection bags in said base portion;

said base portion further having a first longitudinal wall disposed at an end of said base portion where said shell portion is pivotally attached thereto, and further having a second longitudinal wall disposed at on end of said base portion opposite of said first longitudinal wall;

said base portion further having a plurality of parallel, spaced-apart channels disposed along said longitudinal axis of said base portion and configured for each channel of said plurality of channels to abutably receive one of said plurality of oxygenated blood collection bags;

said base portion further having a plurality of slot means disposed in said second longitudinal wall of said base portion and also disposed contiguously of said plurality of channels, with each slot of said plurality of slots configured to receive a portion of flexible tubing of said plurality flexible tubing, with each of said portions of flexible tubing of said plurality of flexible tubing emanating from said plurality of oxygenated blood collection bags disposed in said plurality of channels;

said base portion further including warming means interconnected with an external power source and configured to abutably receive said plurality of oxygenated blood collection bags for maintaining said sequestered blood at a temperature of 37° C.; and flow promoting means applied to said flexible catheter tubing for urging flow of said patient's blood from said flexible catheter tubing to said plurality of oxygenated blood collection bags.

22. The closed circuit autologous blood sequestration reservoir system recited in claim 21, wherein said flow promoting means comprises placing said patient in a position in which an end of said table is raised to lower said patient's legs relative to said patient's head so that said patient's blood is gravity-driven from said flexible catheter tubing to said plurality of oxygenated blood collection bags.

23. The closed circuit autologous blood sequestration reservoir system recited in claim 21, wherein said flow promoting means comprises pump means disposed adjacent said housing and in fluid communication with said valve assembly.

24. The closed circuit autologous blood sequestration reservoir system recited in claim 21, wherein said valve assembly comprises a plurality of stopcocks configured so that each of said plurality of stopcocks receives one tube of said plurality of flexible tubing.

25. The closed circuit autologous blood sequestration reservoir system recited in claim 21, wherein said tube inlay assembly includes a plurality of spaced-apart orifices configured to transport oxygen from said oxygen source to said sequestered blood.

26. The closed circuit autologous blood sequestration reservoir system recited in claim 21, wherein each of said plurality of oxygenated blood collection bags comprises a pressure-relief means for discharging excess oxygen without discharging said oxygen from said oxygenated sequestered blood.

27. The closed circuit autologous blood sequestration reservoir system recited in claim 21, wherein said portable housing means comprises agitation means rotatably attached to said housing means for rotating each of said plurality of oxygenated blood collection bags within each of said corresponding plurality of slot means.

28. The closed circuit autologous blood sequestration reservoir system recited in claim 21, wherein each of said plurality of oxygenated blood collection bags comprises auxiliary pump means in fluid communication with said anticoagulant means for controlling dilution of said oxygenated sequestered blood.

* * * * *